US 9,913,817 B2
Mar. 13, 2018

(12) United States Patent
Baroni et al.

(54) METHODS FOR PREVENTING OR REDUCING COLON CARCINOGENESIS

(71) Applicant: Nogra Pharma Limited, Dublin (IE)

(72) Inventors: Sergio Baroni, Villa d'adda (IT); Salvatore Bellinvia, Mendrisio (CH); Francesca Viti, Salorino (CH)

(73) Assignee: Nogra Pharma Limited, Dublin (IE)

( * ) Notice: Subject to any disclaimer, the term of this patent is extended or adjusted under 35 U.S.C. 154(b) by 0 days.

(21) Appl. No.: 15/088,654

(22) Filed: Apr. 1, 2016

(65) Prior Publication Data

US 2017/0056349 A1    Mar. 2, 2017

Related U.S. Application Data

(63) Continuation of application No. 13/131,978, filed as application No. PCT/EP2009/008631 on Dec. 3, 2009, now abandoned.

(60) Provisional application No. 61/222,281, filed on Jul. 1, 2009, provisional application No. 61/157,674, filed on Mar. 5, 2009.

(30) Foreign Application Priority Data

Dec. 5, 2008 (EP) ..................................... 08425775

(51) Int. Cl.
| | | |
|---|---|---|
| A61K 31/196 | (2006.01) |
| A61K 31/136 | (2006.01) |
| A61K 31/166 | (2006.01) |
| A61K 31/343 | (2006.01) |
| A61K 31/357 | (2006.01) |
| A61K 9/00 | (2006.01) |

(52) U.S. Cl.
CPC .......... *A61K 31/196* (2013.01); *A61K 9/0014* (2013.01); *A61K 31/136* (2013.01); *A61K 31/166* (2013.01); *A61K 31/343* (2013.01); *A61K 31/357* (2013.01)

(58) Field of Classification Search
None
See application file for complete search history.

(56) References Cited

U.S. PATENT DOCUMENTS

| | | |
|---|---|---|
| 3,211,610 A | 10/1965 | Rogers |
| 3,444,232 A | 5/1969 | Bernstein |
| 4,036,951 A | 7/1977 | Halpern et al. |
| 4,348,223 A | 9/1982 | Grove |
| 4,404,215 A | 9/1983 | Vincent et al. |
| 4,429,152 A | 1/1984 | Gries et al. |
| 4,720,506 A | 1/1988 | Munakata et al. |
| 4,869,913 A | 9/1989 | Gries et al. |
| 4,933,330 A | 6/1990 | Jorgensen et al. |
| 5,262,549 A | 11/1993 | Telfer et al. |
| 5,302,751 A | 4/1994 | Manimaran et al. |
| 5,519,014 A | 5/1996 | Borody |
| 5,594,015 A | 1/1997 | Kurtz et al. |
| 5,594,151 A | 1/1997 | Stolowitz |
| 6,114,382 A | 9/2000 | Moretti |
| 6,194,627 B1 | 2/2001 | Geissler et al. |
| 6,326,364 B1 | 12/2001 | Lin et al. |
| 6,403,656 B1 | 6/2002 | Rivier et al. |
| 6,583,128 B2 | 6/2003 | Ekwuribe et al. |
| 6,602,869 B1 | 8/2003 | Galey et al. |
| 6,844,003 B2 | 1/2005 | Galey et al. |
| 6,884,821 B1 | 4/2005 | Shinoda et al. |
| 6,903,082 B2 | 6/2005 | Ekwuribe et al. |
| 7,049,342 B2 | 5/2006 | Miyachi et al. |
| 7,098,025 B1 | 8/2006 | Auwerx et al. |
| 7,176,204 B2 | 2/2007 | Miyachi et al. |
| 7,425,578 B2 | 9/2008 | Ekwuribe et al. |
| 7,429,676 B2 | 9/2008 | Woltering et al. |
| 7,749,980 B2 | 7/2010 | Plourde, Jr. et al. |
| 7,998,474 B2 | 8/2011 | Kelly |
| 8,030,520 B2 | 10/2011 | Sundermeier et al. |
| 8,138,357 B2 | 3/2012 | Naccari et al. |
| 8,153,693 B2 | 4/2012 | Baroni et al. |
| 8,153,841 B2 | 4/2012 | Naccari et al. |
| 8,450,506 B2 | 5/2013 | Naccari et al. |
| 8,501,806 B2 | 8/2013 | Baroni et al. |
| 8,710,100 B2 | 4/2014 | Naccari et al. |
| 8,754,127 B2 | 6/2014 | Baroni et al. |
| 8,796,334 B2 | 8/2014 | Baroni et al. |
| 9,133,099 B2 | 9/2015 | Naccari et al. |
| 9,345,680 B2 | 5/2016 | Naccari et al. |

(Continued)

FOREIGN PATENT DOCUMENTS

| | | |
|---|---|---|
| EP | 0055689 A1 | 7/1982 |
| EP | 0102833 A1 | 3/1984 |

(Continued)

OTHER PUBLICATIONS

Ahnfelt-Ronne et al. (1990) "Clinical Evidence Supporting the Radical Scavenger Mechanism of 5-Aminosalicylic Acid," Gastroenterology, 98(5 Pt 1):1162-9.

Allgayer (2003) "Review Article: Mechanisms of Action of Mesalazine in Preventing Colorectal Carcinoma in Inflammatory Bowel Disease," Aliment Pharmacol Ther, 18(Suppl. 2):10-4.

Ameho et al., (1997) 'Prophylactic Effect of Dietary Glutamine Supplementation on Interleukin 8 and Tumor Necrosis Factor Alpha Production in Trinitrobenzene Sulphonic Acid Induced Colitis,' Gut, 41(4):487-93.

(Continued)

*Primary Examiner* — Craig D Ricci
(74) *Attorney, Agent, or Firm* — Goodwin Procter LLP

(57) ABSTRACT

The present invention is directed in part to methods of preventing or reducing colon carcinogenesis comprising administering to a patient at risk of colorectal cancer, a pharmaceutical preparation comprising disclosed chemopreventive. In another aspect, the invention is directed to methods attenuation of oxygen free radicals comprising administrating to a patient in need thereof an antioxidant effective amount of a compound represented by formula I, IIa or IIb as disclosed herein.

2 Claims, 7 Drawing Sheets

(56) References Cited

U.S. PATENT DOCUMENTS

| | | |
|---|---|---|
| 9,511,041 B2 | 12/2016 | Baroni et al. |
| 9,561,202 B2 | 2/2017 | Naccari et al. |
| 9,682,050 B2 | 6/2017 | Baroni et al. |
| 9,682,923 B2 | 6/2017 | Baroni et al. |
| 2003/0113815 A1 | 6/2003 | Houseknecht et al. |
| 2003/0133875 A1 | 7/2003 | Kelly |
| 2003/0220374 A1 | 11/2003 | Needleman |
| 2003/0229083 A1 | 12/2003 | Debnath et al. |
| 2004/0034067 A1 | 2/2004 | MacPhee |
| 2004/0115127 A1 | 6/2004 | Wright et al. |
| 2004/0132110 A1 | 7/2004 | Desreumaux et al. |
| 2006/0159648 A1 | 7/2006 | Davis et al. |
| 2006/0177444 A1 | 8/2006 | Horizoe |
| 2006/0270635 A1 | 11/2006 | Wallace et al. |
| 2007/0086967 A1 | 4/2007 | MacDonald |
| 2007/0149804 A1 | 6/2007 | Woltering et al. |
| 2009/0048343 A1 | 2/2009 | Naccari et al. |
| 2009/0118357 A1 | 5/2009 | Naccari et al. |
| 2010/0305077 A1 | 12/2010 | Baroni et al. |
| 2011/0105748 A1 | 5/2011 | Bhuniya et al. |
| 2011/0152225 A1 | 6/2011 | Baroni et al. |
| 2011/0288058 A1 | 11/2011 | Baroni et al. |
| 2011/0288177 A1 | 11/2011 | Baroni et al. |
| 2012/0053244 A1 | 3/2012 | Baroni et al. |
| 2012/0053245 A1 | 3/2012 | Baroni et al. |
| 2012/0157417 A1 | 6/2012 | Baroni et al. |
| 2012/0316230 A1 | 12/2012 | Naccari et al. |
| 2013/0005813 A1 | 1/2013 | Naccari et al. |
| 2015/0045436 A1 | 2/2015 | Naccari et al. |
| 2015/0051285 A1 | 2/2015 | Baroni et al. |
| 2015/0087678 A1 | 3/2015 | Baroni et al. |
| 2015/0087708 A1 | 3/2015 | Baroni et al. |
| 2015/0148418 A1 | 5/2015 | Baroni et al. |
| 2015/0250749 A1 | 9/2015 | Giuliani et al. |
| 2015/0265514 A1 | 9/2015 | Giuliani et al. |
| 2015/0265562 A1 | 9/2015 | Naccari et al. |
| 2015/0265563 A1 | 9/2015 | Naccari et al. |
| 2016/0338927 A1 | 11/2016 | Baroni et al. |
| 2017/0172956 A1 | 6/2017 | Baroni et al. |

FOREIGN PATENT DOCUMENTS

| | | |
|---|---|---|
| EP | 0279096 A2 | 8/1988 |
| EP | 0291159 A2 | 11/1988 |
| EP | 0352826 A2 | 1/1990 |
| EP | 0623104 B1 | 8/1997 |
| EP | 0938459 B1 | 7/2002 |
| EP | 1285908 A1 | 2/2003 |
| EP | 1348698 A1 | 10/2003 |
| EP | 0554291 B1 | 12/2003 |
| EP | 1373906 A1 | 1/2004 |
| EP | 1389044 A1 | 2/2004 |
| EP | 1607103 A1 | 12/2005 |
| EP | 1274407 B1 | 3/2006 |
| EP | 1801093 B1 | 3/2009 |
| EP | 1448995 B1 | 1/2011 |
| EP | 2298321 A1 | 3/2011 |
| EP | 2107047 B1 | 9/2011 |
| GB | 767788 A | 2/1957 |
| GB | 1359560 | 7/1974 |
| JP | 2003-516310 A | 5/2003 |
| JP | 3425441 B2 | 7/2003 |
| JP | 2004-528329 A | 9/2004 |
| JP | 2005-510733 A | 4/2005 |
| JP | 2009-242399 A | 10/2009 |
| WO | WO-1992/06690 A1 | 4/1992 |
| WO | WO-1993/014056 A1 | 7/1993 |
| WO | WO-1994/00135 A1 | 1/1994 |
| WO | WO-1995/31194 A1 | 11/1995 |
| WO | WO-1996/030016 A2 | 10/1996 |
| WO | WO-1997/025042 A1 | 7/1997 |
| WO | WO-1998/006387 A2 | 2/1998 |
| WO | WO-1998/43081 A1 | 10/1998 |
| WO | WO-1999/015520 A1 | 4/1999 |
| WO | WO-2000/59866 A1 | 10/2000 |
| WO | WO-2000/062766 A2 | 10/2000 |
| WO | WO-2001/02388 A1 | 1/2001 |
| WO | WO-2001/25181 A1 | 4/2001 |
| WO | WO-2001/79153 A1 | 10/2001 |
| WO | WO-2002/046161 A1 | 6/2002 |
| WO | WO-2002/077651 A1 | 10/2002 |
| WO | WO-2002/085123 A1 | 10/2002 |
| WO | WO-2002/095393 A2 | 11/2002 |
| WO | WO-2003/033481 A1 | 4/2003 |
| WO | WO-2003/046580 A1 | 6/2003 |
| WO | WO-2003/048116 A2 | 6/2003 |
| WO | WO-2004/073622 A2 | 9/2004 |
| WO | WO-2005/012280 A1 | 2/2005 |
| WO | WO-2005/040102 A2 | 5/2005 |
| WO | WO-2005/072113 A2 | 8/2005 |
| WO | WO-2005/084658 A1 | 9/2005 |
| WO | WO-2006/072175 A1 | 7/2006 |
| WO | WO-2007/010514 A2 | 1/2007 |
| WO | WO-2007/010516 A2 | 1/2007 |
| WO | WO-2007/096148 A1 | 8/2007 |
| WO | WO-2008/094618 A2 | 8/2008 |
| WO | WO-2008/104557 A1 | 9/2008 |
| WO | WO-2009/025854 A1 | 2/2009 |
| WO | WO-2009/080828 A2 | 7/2009 |
| WO | WO-2010/063470 A2 | 6/2010 |
| WO | WO-2010/063472 A1 | 6/2010 |
| WO | WO-2010/091892 A2 | 8/2010 |
| WO | WO-2010/091894 A2 | 8/2010 |
| WO | WO-2013/012662 A2 | 1/2013 |
| WO | WO-2013/064153 A1 | 5/2013 |
| WO | WO-2013/117744 A9 | 8/2013 |
| WO | WO-2013/156413 A1 | 10/2013 |
| WO | WO-2013/178815 A1 | 12/2013 |
| WO | WO-2013/178816 A1 | 12/2013 |
| WO | WO-2014/041140 A1 | 3/2014 |
| WO | WO-2014/041141 A1 | 3/2014 |
| WO | WO-2016/154730 A1 | 10/2016 |
| WO | WO-2016/202341 A1 | 12/2016 |

OTHER PUBLICATIONS

Australian Examination Report dated Jan. 31, 2014, for Application No. 2009321722 (9 pages).

Baker et al., (1962) "Potential Anticancer Agents. LXXVIII Nonclassical Antimetabolites. IV. Synthesis of Compounds Related to 4-(Iodoacetamido) Salicylie Acid, an Exo-Alkylating Irreversible Inhibitor," J Org Chem, 27(9):3283-95.

Baz et al. (2003) 'Oxidant / Antioxidant Status in Patients with Psoriasis,' Yonsei Med J, 44(6):987-90.

Behshad et al., (2008) 'A Retrospective Case Series Review of the Peroxisome Proliferator-Activated Receptor Ligand Rosiglitazone in the Treatment of Atopic Dermatitis,' Arch Dermatol, 144(1):84-8.

Beilstein Database Beistein Institute zur Forderung der Chemischen Wissenschaften, Frankfurt an Main, DE XP002413839, Accession No. 2092096, J. Med. Chem., 22: 589 (1979).

Beilstein Database, Beilstein Institute for Organic Chemistry, Frankfurt an Main, DE, retrieved from XFIRE, Accession No. brn 2208094, J. Am. Chem. Soc., 68: 2335, 2338 (1946).

Beilstein Database, Beilstein Institute for Organic Chemistry, Frankfurt an Main, DE, retrieved from XFIRE, Accession No. brn 2803076, J. Org. Chem., 14: 1013, 1018 (1949).

Beilstein Database, Beilstein Institute for Organic Chemistry, Frankfurt an Main, DE, retrieved from XFIRE, Accession No. brn 3199913, Chem. Ber., 46: 3978 (1913).

Beilstein Database, Beilstein Institute for Organic Chemistry, Frankfurt an Main, DE, retrieved from XFIRE, Accession No. brn 3200601, J. Chem. Soc., pp. 104, 111 (1935).

Beilstein Database, Beilstein Institute for Organic Chemistry, Frankfurt an Main, DE, retrieved from XFIRE, Accession No. brn 3268495, Justus Liebigs Ann. Chem., 463:60 (1924).

Beilstein Database, Beilstein Institute for Organic Chemistry, Frankfurt an Main, DE, retrieved from XFIRE, Accession No. brn 3296969, Chem. News J. Ind. Sci, 36: 269 (1877).

Beilstein Database, Beilstein Institute for Organic Chemistry, Frankfurt an Main, DE, retrieved from XFIRE, Accession No. pcrn 859019, U.S. Pat. No. 4,429,152 A (Jan. 1984).

(56) References Cited

OTHER PUBLICATIONS

Beilstein Database, Beilstein Institute for Organic Chemistsry, Frankfurt an Main, DE, retrieved from XFIRE, Accession No. brn 3199917, Chem. Ber., 46: 288 (1913).
Beilstein Database, Beilstsein Institute for Organic Chemistry, Frankfurt an Main, DE, retrieved from XFIRE, Accession No. brn 3242057, Chem. Ber., 74: 500, 517 (1941).
Beilstein Database, Beistein Institut zur Forderung der Chemischen Wissenschaften, Frankfurt an Main, DE, XP002413837, Accession No. 2367395, Chem. Ber., 87: 179-181 (1954.).
Beilstein Database, Beistein Institut zur Forderung der Chemischen Wissenschaften, Frankfurt an Main, DE, XP002413838, Accession No. 2839685, J. Am. Chem Soc., 73: 903-904 (1951).
Beilstein Database, Beistein Institut zur Forderung der Chemischen Wissenschaften, Frankfurt an Main, DE, XP002413840, Accession No. 3031462, Bull Soc. Chim Belg., 61: 310-320 (1952).
Beilstein Database, Beistein Institut zur Forderung der Chemischen Wissenschaften, Frankfurt an Main, DE, XP002413842, Accession No. 3259704, Justus Liebigs Ann Chem, 429: 173 (1922).
Beilstein Database, Beistein Institut zur Förderrung der Chemischen Wisssenschaften, Frankfurt an Main, DE, XP002413836, Accession No. 1869425, J. Labelled Compd Radiopharm, 44: S225-S227 (2001).
Beilstein Database, Beisten Insstitut zur Forderung der Chemischen Wissenschaften, Frankfurt an Main, DE, XP002413843, Accession No. 3530419, Justus Liebigs Ann Chem, 429: 164 (1922).
Beilstein Database, Beisten Institut zur Forderung der Chemischen Wissenschaften, Frankfurt an Main, DE, XP002413841, Accession No. 2641495, J. Org. Chem., 27: 3283-3295 (1962).
Bickers et al., (2006) 'Oxidative Stress in the Pathogenesis of Skin Disease,' J Invest Dermatol, 126(2):2565-75.
Bongartz et al., (2005) 'Treatment of Active Psoriatic Arthritis with the PPARγ Ligand Pioglitazone: An Open-Label Pilot Study,' Rheumatology, 44(1):126-9.
Broadwith (2009) "Enzyme Binds Both Sides of the Mirror," Chem World, Nov. 6, 2009, https://www.chemistryworld.com/news/enzyme-binds-both-sides-of-the-mirror/1016647.article (2 pages).
Brown and Joyeau, (1979), 'Use of p-Aminophenyl D and L-Lactic Acids and p-Aminophenyl Pyruvic Acid as Effectors in the Affinity Chromatography of Lactate Dehydrogenase,' Biochimie, 61(3):437-42 (Abstract only).
Brown et al., (1978) "Chimie Organique," C.R. Acad. Sc. Paris, t. 287:125-8.
Brunton et al., (1997) "A Role of Epidermal Growth Factor Receptor, c-Src and Focal Adhesion Kinase in an in vitro Model for the Progression of Colon Cancer," Oncogene, 14( 3):283-93.
Bull (2003) "The Role of Peroxisome Proliferator-Activated Receptor y in Colon Cancer and Inflammatory Bowel Disease," Arch Pathol Lab Med, 127(9):1121-3.
Clark et al., (1989) "Validation of the General Purpose Tripos 5.2 Field," J. Comput Chem, 10(8):982-1012.
Collino et al., (2006) "Modulation of the Oxidative Stress and Inflammatory Response by PPAR-gamma Agonists in the Hippocampus of Rats Exposed to Cerebral Ischemia/Reperfusion," Eur J Pharmacol, 530(1-2):70-80.
Corse et al., (1948) "Biosythesis of Penicillins" J Am Chem Soc, 70(9):2837-43.
Database CA [Online] Chemical Abstracts Service, Columbus Ohio, US; Database Accession No. 67:50608, Abstract of Baker et al.: "Irreversible Enzyme Inhibitors. LXXXVII. Hydrophobic Bonding to dihydrofolic reductase. 9. Mode of Binding of m-aryloxyalkyl groups on, 6-diamino-1,2-dihydro-2,2-dimethyl-1-phenyl-s-triazine", (1967).
Database CA [Online] Chemical Abstracts Service, Columbus, Ohio, US, Database Accession No. 107:235800, Abstract of Cleary, et al., "Methylenecyclopropane rearrangement as a probe for free radical substituent effects . . . sigma . . . bul. Values for commonly encountered conjugating and organometallic groups", (1987).
Database CA [Online] Chemical Abstracts Service, Columbus, Ohio, US, Database Accession No. 111:153586, Abstract of Gonzalez, et al., ".alpha.-Amino carbanions. A second generation formamidine for facile deprotonation leading to .alpha.-quaternary substitution", (1989).
Database CA [Online] Chemical Abstracts Service, Columbus, Ohio, US, Database Accession No. 119:95018, Abstract of Yoon, et al., "Reduction of nitro compounds with borohydride exchange resin—nickel acetate", (1993).
Database CA [Online] Chemical Abstracts Service, Columbus, Ohio, US, Database Accession No. 131:144358, Abstract of Lamy-Pitara, et al., "Selective Catalytic Hydrogenation of Unsaturated Derivatives of Nitrobenzene in Alcoholic Media", (1999).
Database CA [Online] Chemical Abstracts Service, Columbus, Ohio, US, Database Accession No. 50:52519, Abstract of Pratt, et al., "Reaction rates by distillation. VI. The etherification of benzyl and related alcohols", (1956).
Database CA [Online] Chemical Abstracts Service, Columbus, Ohio, US, Database Accession No. 8:526, Abstract of Schepss, "Electrolytic reduction of aldehydes", (1914).
Database CA [Online] Chemical Abstracts Service, Columbus, Ohio, US, Database Accession No. 2010:351508, Abstract of Baroni, et al., "Compounds for the selective treatment of intestinal immuninflammatory component of the celiac disease", (2007).
Database CA [Online] Chemical Abstracts Service, Columbus, Ohio, US, Database Document No. 118:101608, Accession No. 1993:101608, Abstract of Breuer, et al., "An efficient synthesis of ethyl 3'-aminocinnamate", (1992).
Database CA [Online] Chemical Abstracts Service, Columbus, Ohio, US: Database Accession No. 96:19761, Abstract of Macek et al., "Studies on Local Anesthetics LXXIV. Basic esters of o-(m-)(alkoxymethyl)carbanilic acids", (1981).
Database CA [Online] Chemical Abstracts Service, Columbus, Ohio, US; Database Accession No. 105:24135, Abstract of Wulff, et al., "Chemistry of binding sites. VI. On the suitability of various aldehydes and ketones as binding sites for monoalcohols", (1986).
Database CA [Online] Chemical Abstracts Service, Columbus, Ohio, US; Database Accession No. 110:194186, Abstract of Pei et al., "A Lewis acid catalyst supported by polymers-styrene-methyl methacrylate copolymer-titanium tetrachloride complex preparation and uses in organic synthesis", (1989).
Database CA [Online] Chemical Abstracts Service, Columbus, Ohio, US; Database Accession No. 112:157479, Abstract of Joshi et al., "Catalysis by heteropoly acids: some new aspects", (1989).
Database CA [Online] Chemical Abstracts Service, Columbus, Ohio, US; Database Accession No. 121:204747, Abstract of Yang et al., "Photosolvolysis of 2-aminobenzyl alcohol in aqueous solution", (1994).
Database CA [Online] Chemical Abstracts Service, Columbus, Ohio, US; Database Accession No. 131:228419, Abstract of Engell et al., "The Decomposition of methyl hemiacetals of benzaldehyde in aqueous solution: a study of the effect of aromatic substitution", (1999).
Database CA [Online] Chemical Abstracts Service, Columbus, Ohio, US; Database Accession No. 135:180359, Abstract of Pitts et al., "Indium metal as a reducing agent in organic synthesis", (2001).
Database CA [Online] Chemical Abstracts Service, Columbus, Ohio, US; Database Accession No. 49:68907, Abstract of Mann, et al., "The action of magnesium and of Grignard reagents on certain benzyl ethers. II. The action of Grignard reagents on .omicron.-, m-, and p-(methoxy- and phenoxymethyl) anilines", (1954).
Database CA [Online] Chemical Abstracts Service, Columbus, Ohio, US; Database Accession No. 66:37529, Abstract of Minisci, et al., "Orientation in the radical amination of aromatic compounds with N-chlorodimethylamine-competition between nuclear and benzylic attack", (1966).
Database CA [Online] Chemical Abstracts Service, Columbus, Ohio, US; Database Accession No. 84:4573, Abstract of Gale, et al., "Amidomethylation of some N,N-dialkylanilines (Tscherniac-Einhorn reaction)", (1975).
Database CA Registry [Online] Chemical Abstracts Service, Columbus, Ohio, US; Database Accession No. 1001756-73-5, Abstract & "Allichem Catalog" Jun. 3, 2009; XP002595814, (2008).

(56) References Cited

OTHER PUBLICATIONS

Database Caplus Chemical Abstracts Service, Columbus, Ohio, US; Database Accession No. 1913:10241, Abstract of Heller: Berichte der Deutschen Chemischen Gesellschaft (1913), 46:280-294.
Database Caplus Chemical Abstracts Service, Columbus, Ohio, US; Database Accession No. 1949:23214, Abstract of Tomcsik et al.: Helvetica Chimica Acta (1949), 32:31-34.
Database Caplus Chemical Abstracts Service, Columbus, Ohio, US; Database Accession No. 1955:19868, Abstract of Mann et al.: Chemistry & Industry (London, United Kingdom) (1954) 373-374.
Database Caplus Chemical Abstracts Service, Columbus, Ohio, US; Database Accession No. 1979:18291, Abstract of Brown et al.: "Affinity Chromatography of L-lactate dehydrogenase (LDH) on Synthetic Supports. Preparation and Immobilization of D- and L-p-aminophenyllactic Acids, New Effectors of LDH." Comptes Rendus des Seances de l'Academic des Scie. 287(4):125-128 (1978).
Database Caplus Chemical Abstracts Service, Columbus, Ohio; Database Accession No. 1925:25469, Abstract of Sherwin: "Acetylation as a Physiologic Reaction." Proceedings of the Society for Experimental Biology and Medicine (1924), 22:182.
Database Caplus Chemical Abstracts Service, Columbus, Ohio; Database Accession No. 1967:490291, Abstract of Deljac et al.: "Absolute Configuration of (--) -β-hydroxy-β-(m-hydroxphenyl) propionic acid", Recueill des Travaux Chimiques des Pays-Bas (1967), 68(8):765-768.
Database Chemcats [Online] Chemical Abstracts Service, Columbus, Ohio, US; Accession No. 2058162244, Allichem Product List, Jun. 3, 2009; XP002591674, Feb. 6, 2008.
Delbarre et al., (1964), Chemical Abstracts, vol. 65, Columbus , Ohio, Abstract No. 93711, "Non-steroid Antiinflammatory Substances. I. Derivatives of the 4- and 5-Aminosalicylic Acids".
Deljac et al., (1967) "Absolute Configuration of (-)-β-Hydroxy-β-(m)-Hydroxyphenyl)-Propionic Acid," Recueil des Travaux Chimiques des Pays-Bas, 86:765-8.
Dimon-Gadal et al., (2000) 'Increased Oxidative Damage to Fibroblasts in Skin With and Without Lesions in Psoriasis,' J Invest Dermato1,114(5):984-9.
DiPoï et al., (2004) 'Functions of Peroxisome Proliferator-Activated Receptors (PPAR) in Skin Homeostasis,' Lipids, 39(11):1093-9.
DiPoï et al., (2005) 'Epithelium-Mesenchyme Interactions Control the Activity of Peroxisome Proliferator-Activated Receptor β/δ During Hair Follicle Development,' Mol Cell Biol, 25(5):1696-1712.
Dubuquoy et al., (2002), "Role of peroxisome proliferator-activated receptor γ and retinoid X receptor heterodimer in hepatogastroenterological diseases," Lancet, 360(9343):1410-8.
Dubuquoy et al., (2003) "Impaired Expression of Peroxisome Proliferator-Activated Receptor Gamma in Ulcerative Colitis," Gastroenterology, 124(5):1265-76.
Egan et al., (2003) 'Clinical Pharmacology in Inflammatory Bowel Disease: Optimizing Current Medical Therapy,' *Inflammatory Bowel Disease: From Bench to Bedside*, (2$^{nd}$ Ed, 2003), Stephan R Targan et al. (Eds), Springer Publishingm New York, NY (Publ), pp. 495-521.
Ellis et al., (2007) 'Placebo Response in Two Long-Term Randomized Psoriasis Studies that were Negative for Rosiglitazone,' Am J Clin Dematol, 8(2):93-102.
Examination Report dated Apr. 15, 2011 for Application No. 06 766 083.7-2103 (11 pages).
Fernholz et al., (1992) "Specificity of Antibody-Catalyzed Transesterifications Using Enol Esters: A Comparison with Lipase Reactions," J Org Chem, 57(17):4756-61.
Floch and White, (2006), 'Management of Diverticular Disease is Changing,' World J Gastroenterol, 12(20):3225-8.
Fuenzalida et al., (2007) "Peroxisome Proliferator-activated Receptor Gamma Up-regulates the Bcl-2 Anti-apoptotic Protein in Neurons and Induces Mitochondrial Stabilization and Proection against Oxidative Stress and Apoptosis," J Biol Chem, 282(51):37006-15.
Gampe et al., (2000) "Asymmetry in the PPARγ/RXRα Crystal Structure Reveals the Molecular Basis of Heterodimerization Among Nuclear Receptors," Mol Cell, 5(3):545-55.
Gormin (1989), "Picosecond Transient Absorption Spectra of Aminosalicylates in Confirmation of the Triple Excitation Mechanism," J Phys Chem, 93(16):5979-80.
Guo et al., 92009), "Effect of Uyghur Compound Xipayi Kui Jie an on the Ultrastructure of Small Intestinal Epithelial Cell in Rat Model of Ulcerative Colitis," J Xinjiang Medi Univ, 32(7):893-4.
Harari (2004) "Epidermal Growth Factor Receptor Inhibition Strategies in Oncology," Endocr Relat Cancer, 11(4):689-708.
Harrington et al., (2008) 'A Re-appraisal of Lactose Intolerance,' Int J Clin Pract, 62(10):1541-6.
Husova et al., (2007) "Hepatopathy, Coeliac Disease and Lymphocytic Colitis," Ceska A. Slovenska Gastroenterologie A. Hepatologie—CZ SL Gastroenterol Hepatol, 61(6):309-13.
International Preliminary Report on Patentability and Written Opinion for International Application No. PCT/EP2013/052617 dated Aug. 12, 2014 (5 pages).
International Preliminary Report on Patentability and Written Opinion for International Application No. PCT/EP2013/069062 dated Mar. 17, 2015 (7 pages).
International Preliminary Report on Patentability and Written Opinion for International Application No. PCT/EP2013/069063 dated Mar. 17, 2015 (7 pages).
International Preliminary Report on Patentability and Written Opinion for International Application No. PCT/EP2009/008631, dated Jun. 7, 2011(13 pages).
International Preliminary Report on Patentability and Written Opinion for International Application No. PCT/EP2009/008633, dated Jun. 7, 2011 (6 pages).
International Preliminary Report on Patentability and Written Opinion for International Application No. PCT/EP2010/000935, dated Aug. 16, 2011 (7 pages).
International Preliminary Report on Patentability and Written Opinion for International Application No. PCT/EP2010/000939 dated Aug. 16, 2011 (8 pages).
International Preliminary Report on Patentability and Written Opinion for International Application No. PCT/IE2006/000076 dated Jan. 22, 2008 (10 pages).
International Preliminary Report on Patentability and Written Opinion for International Application No. PCT/EP13/057729 dated Oct. 21, 2014 (6 pages).
International Preliminary Report on Patentability and Written Opinion for International Application No. PCT/EP2008/052354 dated May 22, 2009 (20 pages).
International Preliminary Report on Patentability and Written Opinion for International Application No. PCT/EP2008/068265 dated Apr. 12, 2010 (11 pages).
International Preliminary Report on Patentability and Written Opinion for International Application No. PCT/IE2006/000078 dated Jan. 22, 2008 (14 pages).
International Preliminary Report on Patentability and Written Opinion for International Application No. PCT/IE2006/000078 dated Jan. 26, 2007 (14 pages).
International Search Report for PCT/EP2008/052354 dated Jun. 9, 2008 (6 pages).
International Search Report for PCT/EP2008/068265 dated Aug. 11, 2009 (5 pages).
International Search Report for PCT/EP2009/008631 dated Aug. 19, 2010 (9 pages).
International Search Report for PCT/EP2009/008633, dated Feb. 22, 2010 (4 pages).
International Search Report for PCT/EP2010/000935 dated Aug. 23, 2010 (5 pages).
International Search Report for PCT/EP2010/000939 dated Sep. 20, 2010 (5 pages).
International Search Report for PCT/EP2013/052617 dated Aug. 12, 2014 (4 pages).
International Search Report for PCT/EP2013/057729 dated Jun. 11, 2013 (4 pages).
International Search Report for PCT/EP2013/069062 dated Dec. 10, 2013 (3 pages).

(56) References Cited

OTHER PUBLICATIONS

International Search Report for PCT/EP2013/069063 dated Dec. 20, 2013 (3 pages).
International Search Report for PCT/IE2006/000076 dated Feb. 1, 2007 (5 pages).
Ireland et al. (1992) 'Comparison of 5-Aminosalicylic Acid and N-Acetylaminosalicylic Acid Uptake by the Isolated Human Colonic Epithelial Cell,' Gut, 33(10):1343-7.
Janda et al., (1988) "Antibody Catalysis of Bimolecular Amide Formation," J Am Chem Soc, 110(14):4835-7.
Johnson et al., (2012) 'Intestinal Fibrosis Is Reduced by Early Elimination of Inflammation in a Mouse Model of IBD: Impact of a "Top-Down" Approach to Intestinal Fibrosis in Mice,' Inflamm Bowel Dis, 18(3):460-71.
Jones et al., (1997) "Development and Validation of a Genetic Algorithm for Flexible Docking," J Mol Biol, 267(3):727-48.
Julien et al., (2005) 'Antifibrogenic Role of the Cannabinoid Receptor CB2 in the Liver,' Gastroenterology, 128(3):742-55.
Kari et al., (2003) "Targeting the Epidermal Growth Factor Receptor in Cancer: Apoptosis Takes Center Stage," Cancer Res, 63(1):1-5.
Karnik et al., (2009) 'Hair Follicle Stem Cell-specific PPARγ Deletion Causes Scarring Alopecia,' J Invest Dermatol, 129(5):1243-57.
Kloepper et al., (2008) 'Immunophenotyping of the Human Bulge Region: The Quest to Define Useful in situ Markers for Human Epithelial Hair Follicle Stem Cells and their Niche,' Exp Dermatol, 17(7):592-609.
Koeffler, (2003), "Peroxisome Proliferator-activated Receptpr γ and Cancers," Clin Cancer Res, 9(1):1-9.
Kuenzli and Saurat, (2003) 'Effect of Topical PPARβ/δ and PPARγ Agonists on Plaque Psoriasis: A Pilot Study,' Dermatology, 206(3):252-6.
Lees et al., (2008) 'Analysis of Germline GLI1 Variation Implicates Hedgehog Signaling in the Regulation of Intestinal Inflammatory Pathways,' PLoS Med, 5(12):e239 (15 pages).
Liao et al., (1990) "Therapeutic Effect of Methyl 5-Aminosalicylate on Experimental Ulcerative Colitis in Rabbits," *Acta Pharmacologica Sinica*, 11(1):54-56.
Lin et al., (1998) "An Antibody Transesterase Derived from Reactive Immunization that Utilizes a Wide Variety of Alcohol Substrates," Chem Commun, 10:1075-6.
Lowe, D. (2009) "More Binding Site Weirdness," CORANTE: In the Pipeline, pp. 1-4.
Mangelsdorf et al., (1995) "The Nuclear Receptor Superfamily: The Second Decade," Cell, 83(6): 835-9.
Medow et al., (1990) 'β-Galactosidase Tablets in the Treatment of Lactose Intolerance in Pediatrics,' Am J Dis Child, 144(11):1261-4 (Abstract).
Meek et al., (1969) "Carboxylation of Substituted Phenols in N,N-Dimethylamide Solvents at Atmospheric Pressure," J Chem Eng Data, 14(3):388-91.
Mendelsohn (2001) "The Epidermal Growth Factor Receptor as a Target for Cancer Therapy," Endocr Relat Cancer, 8(1):3-9.
Merck Manual Home Edition, "Ulcerative Colitis", Merck Sharp & Dohme Corp., Copyright © 2004-2011, pp. 1-6 [online] [retrieved on Apr. 19, 2013] Retrieved from http://www.merckmanuals.com/home/print/digestive_disorders/inflammatory_bowel_diseases_ibd/ulcerative_colitis.html.
Michalik and Wahli, (2007) 'Peroxisome Proliferator-activated Receptors (PPARs) in Skin Health, Repair and Disease,' Biochim Biophys Acta, 1771(8):991-8.
Misra et al., (2002) "Phosphorylation of Transcriptional Coactivator Peroxisome Proliferator-Activated Receptor (PPAR)-Binding Protein (PBP). Stimulation of Transcriptional Regulation by Mitogen-Activated Protein Kinase," J Biol Chem, 277(50): 48745-54.
Nolte et al., (1998) "Ligand Binding and Co-Activator Assembly of the Peroxisome Proliferator-Activated Receptor-γ," Nature, 395(6698):137-43.

O'Mahony, et al., (1990) "Coeliac Disease and Collagenous Colitis," Postgrad Med, 66(773):238-41.
Office Action issued in Japanese Patent Application No. 2011-549494 dated Feb. 25, 2014, with English language translation (8 pages).
Osawa et al., (2003) "Peroxisome Proliferator-Activated Receptor γ Ligands Suppress Colon Carcinogenesis Induced by Azoxymethane in Mice," Gastroenterology, 124(2):361-7.
Pedersen et al., (2010) 'Topical Rosiglitazone Treatment Improves Ulcerative Colitis by Restoring Peroxisome Proliferator-Activated Receptor-γ Activity,' Am J Gastroenterol, 105(7):1596-1603 (Abstract).
Pershadsingh et al., (2005) 'Improvement in Psoriasis with Rosiglitazone in a Diabetic and a Nondiabetic Patient,' Skinmed, 4(6):386-90 (Abstract).
Peyrin-Biroulet et al., (2010), 'Peroxisome Proliferator-Activated Receptor Gamma Activation is Required for Maintenance of Innate Antimicrobial Immunity in the Colon,' Proc Natl Acad Sci USA, 107(19):8772-7.
Peyrin-Biroulet, et al. (2007) "Peroxisome Proliferator-Activated Receptor Gamma Functions as an Antibacterial Factor," J Crohns Colitis Suppl, 1(1):2.
Ponchant et al., (1991) Synthesis of 5-[$^{125}$I]-Iodo-Zacopride, a New Probe for 5-HT$_3$ Receptor Binding Sites, Journal of Labelled Compounds and Radiopharmaceuticals, 29(10):1147-55.
Porter and Ihrig, (1923), 'Asymmetric Dyes,' J Am Chem Soc, 45(8):1990-3 (Abstract only).
Ramprasad et al., (2002) 'Sustained-Delivery of Apolipoprotein E-Peptidomimetic Using Multivesicular Liposomes Lowers Serum Cholesterol Levels,' J Control Release, 79(1-3):207-18.
Reifen, Ram, et al. (2004) "5-ASA and Lycopene Decrease the Oxidative Stress and Inflammation Induced by Iron in Rats with Colitis," J Gastroenterol, 3996):514-9.
Result Summary for Study ID No. SB-999910/150 (2002) "A study in patients with Crohn's Disease to evaluate the effect of AVANDIA™ on inflammatory activity mediated by monocytes/macrophages" Retrieved from: download.gsk-clinicalstudyregister.com/files/23093.pdf on May 23, 2012 (2 pages).
Risérus et al., (2008) "Activation of Peroxisome Proliferator-activated Receptor (PPAR) Delta Promotes Reversal of Multiple Metabolic Abnormalities, Reduces Oxidative Stress, and Increases Fatty Acid Oxidation in Moderately Obese Men," Diabetes, 57(NR. 2):332-9.
Ritland et al., (1999) 'Evaluation of 5-Aminosalicylic Acid (5-ASA) for Cancer Chemoprevention: Lack of Efficacy against Nascent Adenomatous Polyps in the Apc$^{Min}$ Mouse,' Clin Cancer Res, 5(4):855-63.
Robertson et al., (1985) 'Structure-Activity Relationships of Arylimidazopyridine Cardiotonics: Discovery and Inotropic Activity of 2-[2-Methoxy-4-(methylsulfinyl)phenyl]-1H-imidazo[4,5-c]pyridine,' J Med Chem, 28(6):717-27.
Rousseaux et al., (2005) "Intestinal Anti-inflammatory Effect of 5-Aminosalicylic Acid is Dependent on Peroxisome Proliferator-Activated Receptor-γ," J Exp Med, 201(8):1205-15.
Rousseaux et al., (2011) 'Preclinical Evaluation of Intestinal Anti-Inflammatory/Analgesic Properties and Phase I Clinical Trial of a New PPAR Agonist Ged-0507-34-Levo,' Gastroenterology, 140(5):S-515 (Abstract).
Rovner (2009) "An Enzyme Reveals an Unexpected Inclusiveness, Protein Binding: Bacterial Enzyme's Active Site Welcomes Both Enantiomers of a Chiral Molecule at the Same Time," Chem Eng News, Nov. 5, 2009 issue, (2 pages) retrieved from http://cen.acs.org/articles/87/web/2009/11/Enzyme-Reveals-Unexpected-Inclusiveness.html?type=paidArticleContent.
Schauber J et al., (2004) 'Histone-Deacetylase Inhibitors Induce the Cathelicidin LL-37 in Gastrointestinal Cells,' Mol Immunol, 41(9):847-54.
Schwab et al., (2007) 'Role of Nuclear Hormone Receptors in Butyrate-Mediated Up-Regulation of the Antimicrobial Peptide Cathelicidin in Epithelial Colorectal Cells,' Mol Immunol, 44(8):2107-14.
Sherwin (1924), "Acetylation as a Physiologic Reaction," Proc Soc Exper Biol & Med, 22:182.

(56) References Cited

OTHER PUBLICATIONS

Speca et al., (2012) 'Cellular and Molecular Mechanisms of Intestinal Fibrosis,' World J Gastroenterol, 18(28):3635-61.
Tanaka et al.,(2001) "Ligands for Peroxisome Proliferator-Activated Receptors α and γ Inhibit Chemically Induced Colitis and Formation of Aberrant Crypt Foci in Rats," Cancer Res., 61(6): 2424-8.
Tosti et al., (2009) 'Treatment Strategies for Alopecia,' Expert Opin Pharmacother, 10(6):1017-26.
Tuleu, et al., (2002) "Colonic Delivery of 4-Aminosalicylic Acid Using Amylose-Ethyl Cellulose-Coated Hydroxypropyl Methyl Cellulose Capsules," Aliment Pharmacol Ther., 167(10):1771-9.
Tursi et al., (2002), 'Long-Term Treatment with Mesalazine and Rifaximin Versus Rifaximin Alone for Patients with Recurrent Attacks of Acute Diverticulitis of Colon,' Digest Liver Dis, 34(7):510-5.
Tursi, (2004), 'Acute Diverticulitis of the Colon—Current Medical Therapeutic Management,' Exp Opin Pharmacother, 5(1):55-9.
Tzameli et al., (2004) 'Regulated Production of a Peroxisome Proliferator-Activated Receptor-γ Ligand During an Early Phase of Adipocyte Differentiation in 3T3-L1 Adipocytes,' J Biol Chem, 279(34):36093-102.
Van't Riet, Bart, et al. (1979) "Synthesis of Hydroxy and Amino-Substituted Benzohydroxamic Acids: Inhibition of Ribonucleotide Reductase and Antitumor Activity," J Med Chem, 22(5) 589-92.
Venkatraman et al., (2004) 'Alpha-Lipoic Acid-Based PPARγ Agonists for Treating Inflammatory Skin Diseases,' Arch Dermatol Res, 296(3):97-104 (Abstract).
Wallace et al., (1989) 'Inhibition of Leukotriene Synthesis Markedly Accelerates Healing in Rat Model of Inflammatory Bowel Disease,' Gastroenterology, 96(1):29-36.
Wang et al., (2002) "Further Development and Validation of Emphirical Scoring Functions for Structure-Based Binding Affinity Prediction," J Comput Aided Mol Des, 16(1):11-26.
Wang et al., (2004) "Cutting Edge: 1,25-Dihydroxyvitamin D3 is a Direct Inducer of Antimicrobial Peptide Gene Expression," The Journal of Immunology, 173(5):2909-12.
Wei et al., (2010) 'Peroxisome Proliferator-Activated Receptor γ: Innate Protection from Excessive Fibrogenesis and Potential therapeutic Target in Systemic Sclerosis,' Curr Opin Rheumatol, 22(6):671-6 (HHS Public Access version of Author Manuscript).
Westin et al., (1998) "Interactions Controlling the Assembly of Nuclear-Receptor Heterodimers and Co-Activators," Nature, 395(6698):199-202.
Williams and Hallett (1989) "Effect of Sulphasalazine and its Active Metabolite, 5-Amino-Salicylic Acid, on Toxic Oxyg en Metabolite Production by Neutrophils," Gut, 30(11):1581-7.
Written Opinion of the International Searching Authority for International Application No. PCT/EP2013/052617 dated Aug. 12, 2014 (4 pages).
Written Opinion of the International Searching Authority for International Application No. PCT/EP2013/069062 dated Dec. 10, 2013 (6 pages).
Written Opinion of the International Searching Authority for International Application No. PCT/EP2013/069063 dated Dec. 29, 2013 (6 pages).
Written Opinion of the International Searching Authority for PCT/EP2008/052354 dated Jun. 9, 2008 (10 pages).
Written Opinion of the International Searching Authority for PCT/EP2008/068265 dated Aug. 11, 2009 (12 pages).
Wu et al., (2006) 'Effects of Rosiglitazone on Expression of TGF-A1 in Experimental Hepatic Fibrosis Rats,' Chin J Gastroenterol Hepatol, 15(2):126-9.
Xu et al., (2001) "Structural Determinants of Ligand Binding Selectivity Between the Peroxisome Proliferator-Activated Receptors," Proc Natl Acad Sci USA, 98(24):13919-24.
Yanai et al., (2004) "Para-Position Derivatives of Fungal Anthelmintic Cyclodepsipeptides Engineered with Streptomyces Venezuelae Antibiotic Biosynthetic Genes," Nat Biotechnol, 22(7):848-55.

Youssef and Badr, (2004) "Role of Peroxisome Proliferator-Activated Receptors in Inflammation Control," J Biomed Biotechnol, 2004(3):156-66.
Yu et al., (2010) 'Peroxisome Proliferator-Activated Receptors Gamma Reverses Hepatic Nutritional Fibrosis in Mice and Suppresses Activation of Hepatic Stellate Cells in vitro,' Int J Biochem Cell Biol, 42(6):948-57.
Zhou et al., (1999) 'Intestinal Metabolism and Transport of 5-Aminosalicylate,' Drug Metab Dispos, 27(4):479-85.
U.S. Appl. No. 13/131,978, Methods for Preventing or Reducing Colon Carcinogenesis, filed Aug. 11, 2011, Published, U.S. 2011-0288058 published on Nov. 24, 2011.
U.S. Appl. No. 13/201,786, Alkylamido Compounds and Uses Thereof, filed Nov. 17, 2011, Granted, U.S. Pat. No. 8,754,127 issued on Jun. 17, 2014.
U.S. Appl. No. 14/255,255, Alkylamido Compounds and Uses Thereof, filed Apr. 17, 2014, Allowed, U.S. Pat. No. 9,511,041 to issue on Dec. 6, 2016.
U.S. Appl. No. 13/131,982, Methods for Preventing or Reducing Colon Carcinogenesis, filed Aug. 11, 2011, Granted, U.S. Pat. No. 8,501,806 issued on Aug. 6, 2013.
U.S. Appl. No. 12/528,522, PPAR-Gamma Agonists for the Induction of Cationic Antimicrobial Peptide Expression as Immunoprotective Stimulants, filed Mar. 4, 2011, Published, U.S. 2011-0152225 published on Jun. 23, 2011.
U.S. Appl. No. 13/201,790, Methods of Treating Hair Related Conditions, filed Nov. 17, 2011, Granted, U.S. Pat. No. 8,796,334 on Aug. 5, 2014.
U.S. Appl. No. 14/314,738, Methods of Treating Hair Related Conditions, filed Jun. 25, 2014, Abandoned, U.S. 2015-0148418 published on May 28, 2015.
U.S. Appl. No. 14/969,939, Methods of Treating Hair Related Conditions, filed Dec. 15, 2015, Pending.
U.S. Appl. No. 11/989,090, Compounds and their Salts Specific to the PPAR Receptors and the EGF Receptors and their Use in the Medical Field, filed Jun. 6, 2008, Granted, U.S. Pat. No. 8,153,841 on Apr. 10, 2012.
U.S. Appl. No. 13/408,439, Compounds and their Salts Specific to the PPAR Receptors and the EGF Receptors and their Use in the Medical Field, filed Feb. 29, 2012, Granted, U.S. Pat. No. 8,710,100 issued on Apr. 29, 2014.
U.S. Appl. No. 14/202,386, Compounds and their Salts Specific to the PPAR Receptors and the EGF Receptors and their Use in the Medical Field, filed Mar. 10, 2014, Granted, U.S. Pat. No. 9,133,099 issued on Sep. 15, 2015.
U.S. Appl. No. 14/671,585, Compounds and their Salts Specific to the PPAR Receptors and the EGF Receptors and their Use in the Medical Field, filed Mar. 27, 2015, Granted, U.S. Pat. No. 9,345,680 issued on May 24, 2016.
U.S. Appl. No. 14/671,579, Compounds and their Salts Specific to the PPAR Receptors and the EGF Receptors and their Use in the Medical Field, filed Mar. 27, 2015, Published, U.S. 2015-0265562 published on Sep. 24, 2015.
U.S. Appl. No. 11/989,033, Compounds and their Salts Specific to the PPAR Receptors and the EGF Receptors and their Use in the Medical Field, filed Jun. 6, 2008, Granted, U.S. Pat. No. 8,138,357 issued on Mar. 20, 2012.
U.S. Appl. No. 13/397,245, Compounds and their Salts Specific to the PPAR Receptors and the EGF Receptors and their Use in the Medical Field, filed Feb. 15, 2012, Granted, U.S. Pat. No. 8,450,506 issued on May 28, 2013.
U.S. Appl. No. 13/785,485, Compounds and their Salts Specific to the PPAR Receptors and the EGF Receptors and their Use in the Medical Field, filed Mar. 5, 2013, Abandoned.
U.S. Appl. No. 12/810,159, Compounds for the Selective Treatment of the Intestinal Immuno-inflammatory Component of the Celiac Disease, filed Aug. 16, 2010, Granted, U.S. Pat. No. 8,153,693 issued on Apr. 10, 2012.
U.S. Appl. No. 13/331,173, Compounds for the Selective Treatment of the Intestinal Immuno-inflammatory Component of the Celiac Disease, filed Dec. 20, 2011, Abandoned, U.S. 2012-0157417 published on Jun. 21, 2012.

(56) References Cited

OTHER PUBLICATIONS

U.S. Appl. No. 14/377,362, Methods of Treating Fibrosis, filed Aug. 7, 2014, Published, U.S. 2015-0087708 published on Mar. 26, 2015.
U.S. Appl. No. 14/394,916, Methods of Treating Lactose Intolerance, filed Oct. 16, 2014, Published, U.S. 2015-0087678 published on Mar. 26, 2015.
U.S. Appl. No. 14/428,048, Methods of Inhibiting Hair Growth, filed Mar. 13, 2015, Published, U.S. 2015-0265514 published on Sep. 24, 2015.
U.S. Appl. No. 14/428,164, Methods of Treating Hair Related Conditions, filed Mar. 13, 2015, Published, US 2015-0250749 published on Sep. 10, 2015.
Azhar, (2010), 'Peroxisome Proliferator-Activated Receptors, Metabolic Syndrome and Cardiovascular Disease,' Future Cardiol, 6(5):657-91 (NIH Public Access Author Manuscript).
Casen Recordati Group, (2016), 'Cleen Ready-to-Use Enema, Summary of Product Characteristics Updated Jun. 16, 2016,' emc+, medicines.org.UK/emc, XP-002763390, <https://www.medicines.org.UK/emc/print-document?documentId=542> [retrieved Oct. 25, 2016] (5 pages).
Casen Recordati Group, (2016), 'Cleen Ready-to-Use Enema,' emc+, medicines.org.UK/emc, XP-002763391, <https://www.medicines.org.UK/emc/history/542#version9> [retrieved Oct. 25, 2016] (2 pages).
Doshi et al., (1997) "A Comparison of Current Acne Grading Systems and Proposal of a Novel System," Int J Dermatol, 36(6):416-8.
Drosner M et al., (2005), 'Photo-Epilation: Guidelines for Care from the European Society for Laser Dermatology (ESLD),' J Cosmet Laser Ther, 7(1):33-8.
European Clinical Trials Register, (2012), entry EudraCT No. 2011-003283-78 [online] Mar. 1, 2012, [retrieved from the internet at <https://www.clinicaltrialsregister.eu/ctr-search/trial/2011-003283-78/IT> on Feb. 1, 2017] European Union Clinical Trials Register, XO—002766683 (6 pages).
Garza LA et al., (2011), 'Bald Scalp in Men with Androgenetic Alopecia Retains Hair Follicle Stem Cells but Lacks CD200-Rich and CD34-Positive Hair Follicle Progenitor Cells,' J Clin Invest, 121(2):613-22.
GlaxoSmithKline. (2008) Scientific Result Summary for Clinical Study ID 49653/292. "A Randomized, Double-Blind, Placebo-Controlled Trial to Assess Three Dose Levels of Rosiglitazone Maleate in the Treatment of Moderate to Severe Plaque Psoriasis," [retrieved from <https://www.gsk-clinicalstudyregister.com/study/49653/292> on Jul. 25, 2017] (3 pages).
International Search Report and Written Opinion of the International Searching Authority for International Application No. PCT/EP2016/079512 dated Feb. 28, 2017 (15 pages).
Lavker RM et al., (2003), 'Hair Follicle Stem Cells,' J Investig Dermatol Symp Proc, 8(1):28-38.
Li L and Xie T, (2005), 'Stem Cell Niche: Structure and Function,' Annu Rev Cell Dev Biol, 21:605-31.
Mager et al., (1979) "Struktur-Wirkungs-Beziehungen bei Salizylsaure- und Benzoesaurederivaten," Zbl. Pharm. 118(Heft 12):1259-75 (concise explanation of relevance attached).
Mandt N et al., (2005), 'Epilation Today: Physiology of the Hair Follicle and Clinical Photo-Epilation,' J Investig Dermatol Symp Proc, 10(3):271-4.
Medline Database, (2013), U.S. National Library of Medicine, Bethesda, MD, XP002763389, Accession No. NLM23651165, Benjamin B et al., 'PPAR-gamma in Ulcerative Colitis: A Novel Target for Intervention,' Curr Drug Targ, 14(12):1501-7.
Oshima H et al., (2001), 'Morphogenesis and Renewal of Hair Follicles from Adult Multipotent Stem Cells,' Cell, 104(2):233-45.
Rousseaux et al., (2010), 'Preclinical and Toxicological Assessments of the Novel Orally Bioavailable PPAR Ligand GED-0507-34-Levo for the Treatment of Inflammatory Bowel Disease,' Gastroenterology 2010 DDW Abstract Supplement, AGA Abstract #1080, 138(5—Suppl 1):S-157.
Troilius A and Troilius C, (1999), 'Hair Removal with a Second Generation Broad Spectrum Intense Pulsed Light Source—A Long Term Follow-up,' J Cutan Laser Ther, 1(3):173-8.
Written Opinion of the International Searching Authority for International Application No. PCT/EP2006/000076 dated Feb. 1, 2007 (9 pages).
U.S. Appl. No. 15/337,707, Alkylamido Compounds and Uses Thereof, filed Oct. 28, 2016, Published US2017-0172956.
U.S. Appl. No. 15/377,013, Compounds and Their Salts Specific to the PPAR Receptors and the EGF Receptors and Their Use in the Medical Field, filed Dec. 13, 2016, Pending.
U.S. Appl. No. 15/593,864, Methods of Treating Fibrosis, filed May 12, 2017, Pending.
U.S. Appl. No. 15/594,023, Methods of Treating Lactose Intolerance, filed May 12, 2017, Pending.

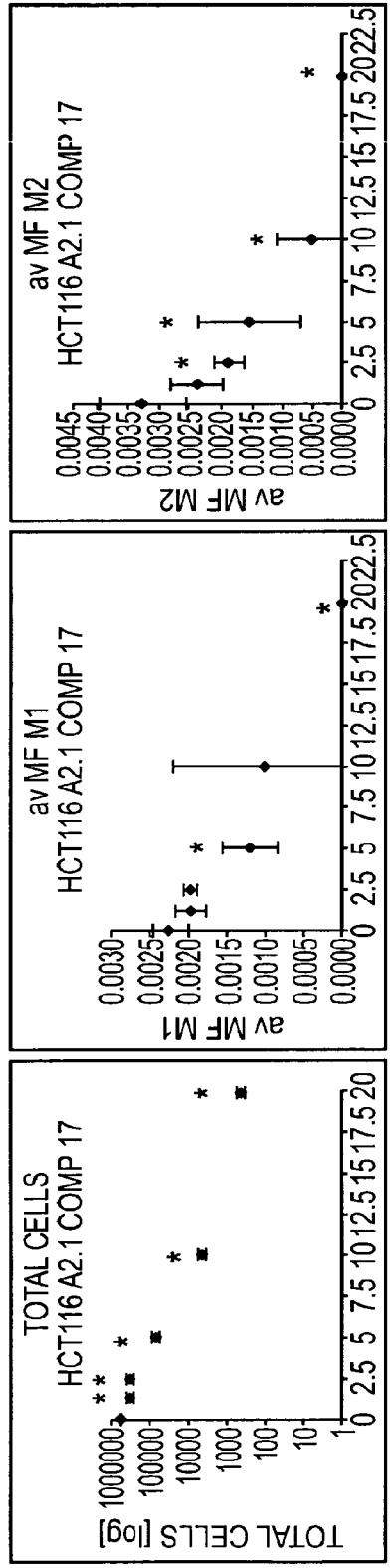
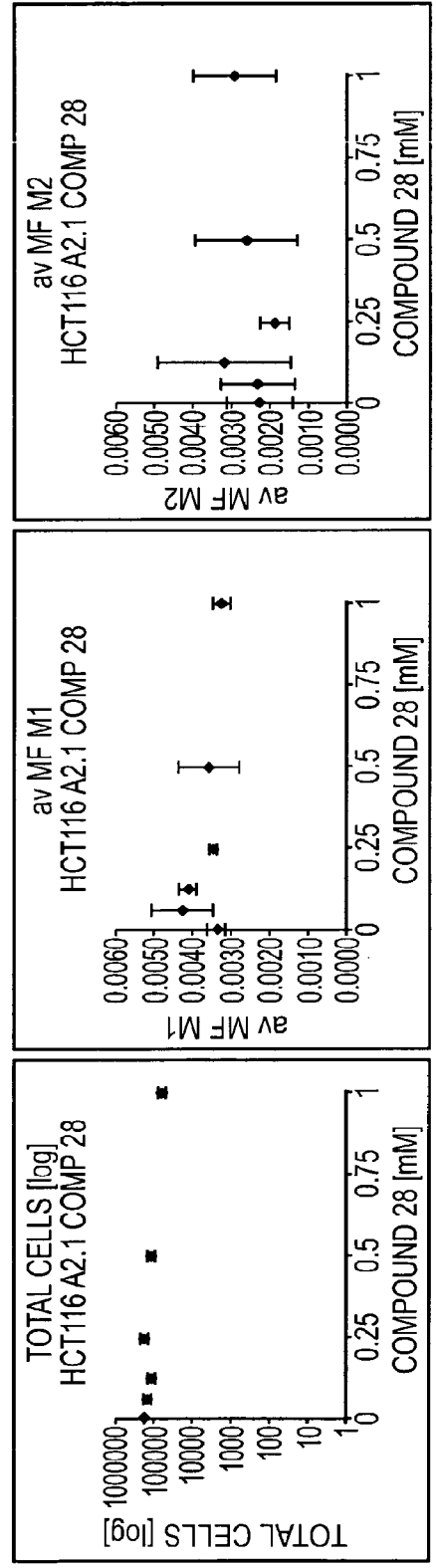
FIG. 3A
FIG. 3B

METHODS FOR PREVENTING OR REDUCING COLON CARCINOGENESIS

RELATED APPLICATIONS

This application is a continuation of U.S. patent application Ser. No. 13/131,978, filed Aug. 11, 2011, which is the national stage filing under 35 U.S.C. § 371 of International Patent Application No. PCT/EP2009/008631, filed Dec. 3, 2009, which claims the benefit of and priority to European Patent Application No. EP08425775.7, filed Dec. 5, 2008; U.S. Provisional Application No. 61/157,674, filed Mar. 5, 2009; and U.S. Provisional Application No. 61/222,281 filed Jul. 1, 2009, the entire disclosure of each of which is hereby incorporated by reference.

BACKGROUND

Colorectal cancer is a serious complication in patients with ulcerative colitis or Crohn's disease. Early age at diagnosis, the extent and severity of colonic disease, the presence of primary sclerosing cholangitis, and/or a family history of cancer represent independent risk factors for the development of colorectal cancer. Aspirin has been found to exert chemopreventive effects in colon cancer, but the mechanism by which it exerts these effects may be complex.

One target for activity of chemopreventive drugs against cancers such as colorectal cancer and solid tumor cancers and adenocarcinomas (such as breast, prostate, lung and heptocellular carcinoma) may be improvement of DNA replication. The fidelity of DNA replication is a product of polymerase accuracy, its proofreading activity, and/or the proficiency of the postreplicational mismatch repair system. Inefficiency of fidelity replication can be a key to the development of human cancer. Chemopreventive drugs that increase such efficiency in colorectal cells could significantly reduce the life-threatening manifestations of cancer and diminish cancer deaths.

The overproduction of reactive oxygen species (ROS) is a common underlying mechanism of many pathologies, as they have been shown to damage various cellular components, including proteins, lipids and DNA. Free radicals, especially superoxide ($O_{(2)}{}^{*-}$), can be generated in quantities large enough to overwhelm endogenous protective enzyme systems, such as superoxide dismutase (SOD). Overproduction of ROS leads to a prooxidant state also known as oxidative stress. Increased levels of ROS and markers of oxidative stress have been consistently found in such cardiovascular diseases as atherosclerosis or hypertension, and studies involving animal models suggest that antioxidant superoxide dismutase mimetics offer a potential new therapeutic approach to the prevention and treatment of chronic obstructive pulmonary disease as well.

The association between compromised antioxidant status, indices of oxidative damage, and other clinical conditions like diabetes mellitus, cardiac disorders such ischemia, various degenerative disorders (e.g. aging) and hair loss is also well documented. Free radicals such as superoxides have also been implicated in a number of skin conditions including photodamage, general aging of the skin, contact dermatitis, and wrinkling. However, there are limited medications available for treating e.g., oxidative damage.

SUMMARY

Also provided herein are methods for attenuating oxygen free radicals comprising administering compounds disclosed herein to a patient. For example, a method of treating fine lines, wrinkles or surface irregularities of the skin, protecting from and/or ameliorating free radical damage to the skin in a subject or patient in need thereof or suffering from same, or a method of treating a patient suffering from unwanted hair loss is provided, comprising administering a pharmaceutical preparation comprising administering (e.g. topically), a chemopreventive agent having the formula I, IIa or IIb:

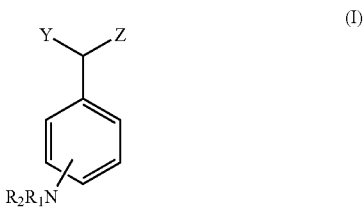

wherein:

$R_1$ and $R_2$, are each independently selected from the group consisting of H and $C_{1-6}$ alkyl; or $R_1$ and $R_2$ together with the nitrogen atom they are bonded to form an aromatic or aliphatic ring with 5 or 6 atoms;

Y and Z are each independently selected from the group consisting of H, OH, COOH, —$OR_3$, —$CH(OR_3)COOH$; and $R_3$ is selected from the group consisting of H, phenyl, benzyl, vinyl, allyl, $C_{1-6}$ alkyl or $C_{1-6}$ alkyl substituted by one or more halogens;

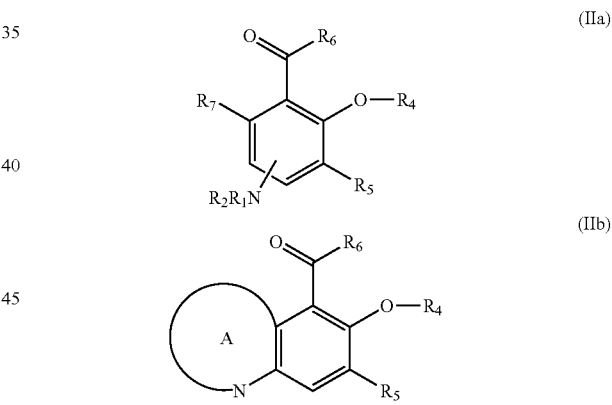

wherein:

$R_1$ and $R_2$ are each independently selected from the group consisting of H and $C_{1-6}$ alkyl; or $R_1$ and $R_2$ together, with the nitrogen atom they are bonded to, form an aromatic or aliphatic ring with 5 or 6 atoms;

$R_6$ is selected from the group consisting of: —$NR_9OH$, OH, and —$OR_9$;

$R_9$ is $C_{1-6}$ alkyl;

$R_4$ is selected from H, halo, phenyl, benzyl, vinyl, allyl, $C_{1-6}$ alkyl or $C_{1-6}$ alkyl substituted by one or more halogens;

$R_5$ and $R_7$ are each independently hydrogen or halo, or $R_4$ and $R_5$, or $R_4$ and $R_6$ together, form a fused heterocyclic ring with 5 or 6 atoms, optionally substituted with halo or $C_{1-6}$ alkyl; and A is a fused heterocyclic ring; or a pharmaceutically acceptable salt thereof.

In another embodiment, a method for attenuation of oxygen free radicals or treating hypoxia is provided, comprising administrating to a patient in need thereof an antioxidant effective amount of a compound represented by formula I, IIa or IIb, as defined above.

Also provided herein are methods of treating a vascular or cardiac disorder, comprising identifying a patient suffering from or at risk of developing said disorder and administering to said patient an effective amount of a compound represented by formula I, IIa, or IIb, as defined above. For example, a cardiac disorder being treated may be chosen from chronic coronary ischemia, arteriosclerosis, congestive heart failure, ischemic or reperfusion related injury, angina, atherosclerosis, myocardial infarction, stroke and myocardial hypertrophy. In another embodiment, a method of treating an autoimmune disorder is provided, wherein the autoimmune disorder may be chosen from, for example, Addison's disease, chronic thyroiditis, dermatomyositis, Grave's disease, multiple sclerosis, systemic lupus erythematosis, psoriasis, or rheumatoid arthritis, and may comprise administering to a patient in need thereof an effective amount of a compound of formula I, IIa, or IIb, as defined above. For example, methods disclosed herein may include methods wherein the patient is human.

This disclosure is directed in part to methods of preventing and/or reducing colon, solid tumor, and/or adenocarcinoma carcinogenesis, e.g. minimizing or prolonging a manifestation of colon cancer comprising administering compounds disclosed herein to a patient, e.g. a human. Such a patient may or may not have, for example, detectable colorectal cancer. In some embodiments, upon or before administration, spontaneous mutation frequency of a colon carcinoma cells are present in the patient. In other embodiments, the patient has Crohn's disease, inflammatory bowel disease, or ulcerative colitis.

Also provided herein are methods for delaying clinical manifestation of a colorectal tumor (or, e.g., a solid tumor or adenocarcinoms) in a patient at risk of colorectal cancer, comprising administering to the patient an effective amount of a chemopreventive compound of a disclosed compound. For example, the delay is at least 1 year as compared to a patient who is not administered a chemopreventive compound. In another embodiment, a patient may have at least about a 30% reduction of the mutation rate of colon carcinoma cells present in the patient.

Also provided herein a methods of treating an age-related disorder selected from the group consisting of: diabetes, cataracts, Alzheimer's disease, Parkinson's disease, macular degeneration, retinal ulcers or retinal vasculitis, comprising administering an effective amount of a composition comprising a compound of formula I, IIa or IIb, as defined above.

These and other aspects and advantages of the invention will become apparent upon consideration of the following figures, detailed description, and claims.

BRIEF DESCRIPTION OF THE DRAWINGS

The invention can be more completely understood with reference to the following drawings.

FIGS. 3A, 3B, and 3C depict the changes in mutation rates of HCT116 A2.1 cells upon incubation with various concentrations (mM) of compounds disclosed herein.

DETAILED DESCRIPTION

Figure 1:
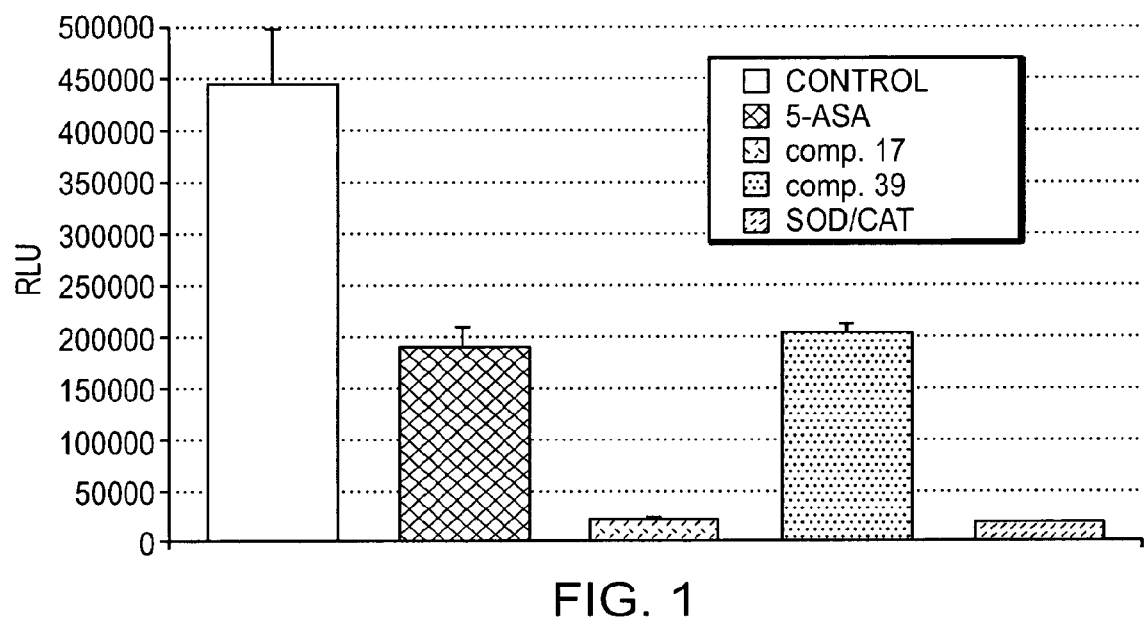
FIG. 1 depicts superoxide scavenging properties of compounds disclosed herein.

The invention is based, in part, upon the discovery that certain compounds disclosed herein have superoxide scavenging potential and/or have the ability to improve the replication fidelity in cancer cells, for example, in colorectal cancer cells. In one aspect, the disclosure is directed to methods of preventing or reducing the incidence of cancer, e.g. colon cancer, in, for example, patients at risk of and/or having risk factors indicating a susceptibility of developing colon cancer. In another aspect, the disclosure is directed to methods of attenuating oxygen free radicals in a patient, and/or methods of treating diseases related to excess of such free radicals. The disclosed methods comprise administering a compound disclosed herein.

Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

A "patient," "subject" or "host" to be treated by the subject method may mean either a human or non-human animal, e.g. a small mammal such as a mouse or rat, and including horse, cow, dog, cat, etc.

The term "therapeutic agent" is art-recognized and refers to any chemical moiety that is a biologically, physiologically, or pharmacologically active substance that acts locally and/or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic effect" is art-recognized and refers to a local and/or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "treating" is art-recognized and refers to curing as well as ameliorating at least one symptom of any condition or disease.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer, e.g. from 1 to 6 carbons. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The definition of each expression, e.g. alkyl, m, n, and the like, when it occurs more than once in any structure, is intended to be independent of its definition elsewhere in the same structure.

Certain compounds contained in compositions of the present invention may exist in particular geometric or stereoisomeric forms. In addition, compounds of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67*th* Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Compounds

Compounds contemplated for use in one or more of the disclosed methods include compounds represented by formula I, or a pharmaceutically acceptable salt, enantiomer or stereoisomer thereof:

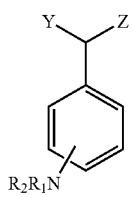

(I)

wherein:

$R_1$ and $R_2$, are each independently selected from the group consisting of H and $C_{1-6}$ alkyl; or $R_1$ and $R_2$ together with the nitrogen atom they are bonded to form an aromatic or aliphatic ring with 5 or 6 atoms which may be optionally substituted;

Y and Z are each independently selected from the group consisting of H, OH, COOH, —$OR_3$, —$CH(OR_3)COOH$; and $R_3$ is selected from the group consisting of H, phenyl, benzyl, vinyl, allyl, $C_{1-6}$ alkyl or $C_{1-6}$ alkyl substituted by one or more halogens.

In an embodiment, Y may be H or COOH. For example, Y may be H and Z may be $CH(OR_3)COOH$, or Y may be COOH and Z maybe —$OR_3$. In some embodiments, $R_3$ may be methyl, ethyl, n-propyl, or isopropyl.

In other embodiments, the $NR_1R_2$ moiety may be in the 4' position or may be in the 3' position. In certain embodiments, $R_1$ and $R_2$ are H.

Exemplary compounds also include those represented by formulas IIa or IIb or a pharmaceutically acceptable salt, enantiomer or stereoisomer of:

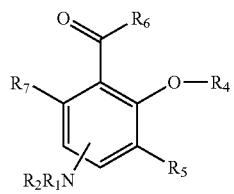

(IIa)

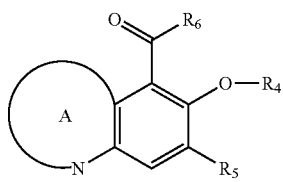

(IIb)

wherein:

$R_1$ and $R_2$ are each independently selected from the group consisting of H and $C_{1-6}$ alkyl; or $R_1$ and $R_2$ together, with the nitrogen atom they are bonded to, form an aromatic or aliphatic ring with 5 or 6 atoms;

$R_6$ is selected from the group consisting of: —NHOH, OH, and —$OR_9$;

$R_9$ is $C_{1-6}$ alkyl;

$R_4$ is selected from H, phenyl, benzyl, vinyl, allyl, $C_{1-6}$ alkyl or $C_{1-6}$ alkyl substituted by one or more halogens;

$R_5$ and $R_7$ are each independently hydrogen or halo, or;

or $R_4$ and $R_5$, or $R_4$ and $R_6$ together, form a fused heterocyclic ring with 5 or 6 atoms, optionally substituted with halo or $C_{1-6}$ alkyl; and A is a fused heterocyclic ring; or a pharmaceutically acceptable salt thereof.

In certain embodiments, the $NR_1R_2$ moiety of formula IIa may be in the 4' position or may be in the 3' position. In certain embodiments, $R_1$ and $R_2$ are H.

$R_9$, in some embodiments, may be methyl, ethyl, n-propyl, or isopropyl.

In some embodiments a compound can be represented by

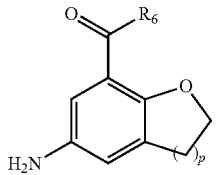 or 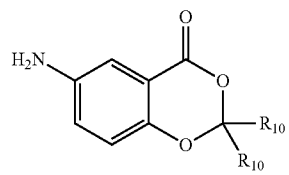

wherein p is 1 or 2, $R_6$ is OH or —$OR_9$, wherein R9 is defined above, and $R_{10}$, independently for each occurrence, is selected from the group consisting of H, halo, or $C_{1-6}$ alkyl, e.g. methyl or ethyl.

Exemplary compounds contemplated herein include:

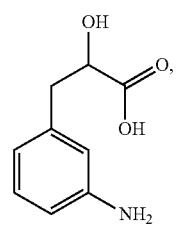

(II)

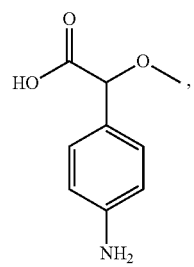

(III)

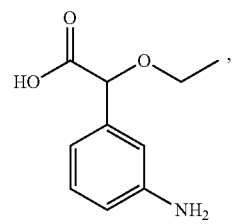

(IV)

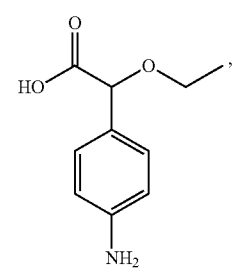

(V)

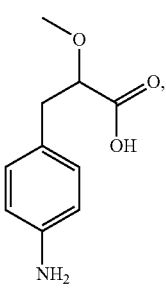
(VI)

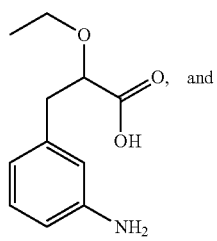
(VIII) and

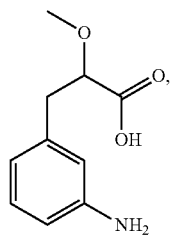
(IX)

or a pharmaceutically acceptable salt thereof.

In some embodiments, contemplated compounds include: 4-amino-N-hydroxy-2-methoxybenzamide (compound 13); 6-methoxy quinoline-5-carboxylic acid (compound 36); 6-methoxy-1,2,3,4-tetrahydroquinoline-5-carboxylic acid (compound 37); 5-diisopropylaminosalicylic acid (compound 38).

Other exemplary compounds include those represented by:

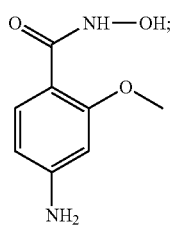
(compound 13)

(compound 14)

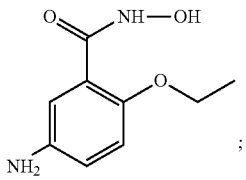
(compound 26)

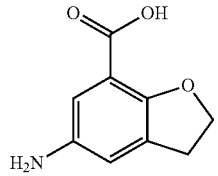
(compound 17)

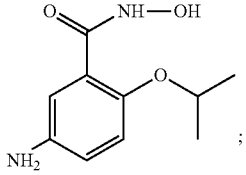
(compound 31)

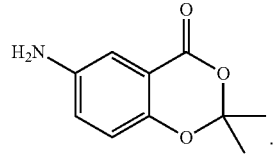
(compound 28)

Compounds contemplated herein include racemic mixtures, and enantiomers of compounds, for example: (±)-2-hydroxy-3-(3'-aminophenyl) propionic acid (compound 20); (±)-2-methoxy-2-(4'-aminophenyl) acetic acid (compound 23); (±)-2-ethoxy-2-(3'-aminophenyl) acetic acid (compound 32); (±)-2-ethoxy-2-(4'-aminophenyl) acetic acid (compound 33); (±)-2-methoxy-3-(4'-aminophenyl) propionic acid (compound 34) "±34" (racemic form); (±)-2-ethoxy-3-(4'-aminophenyl) propionic acid (compound 39); (±)-2-ethoxy-3-(3'-aminophenyl) propionic acid (compound 40).

For example, the compounds used in the methods of the present invention can be enantiomers of the following racemic mixtures: (R,S)-2-hydroxy-2-(3-aminophenyl)acetic acid (compound 10); (R,S)-2-hydroxy-2-(4-aminophenyl)acetic acid (compound 11); (R,S)-2-hydroxy-3-(4'-aminophenyl)propionic acid (compound 21); (R,S)-2-methoxy-2-(3'-aminophenyl)acetic acid (compound 22); (R,S)-2-methoxy-3-(3'-aminophenyl)propionic acid (compound 35); (R,S)-2-methoxy-3-(4-aminophenyl)propionic acid(compound 34), as well as enantiomers, e.g.: (+) 2-S-methoxy-3-(4-aminophenyl)propionic acid(compound 34); (−) 2-R-methoxy-3-(4-aminophenyl)propionic acid(compound 34).

Other racemic type mixtures of compounds contemplated include: e.g. (±)-2-hydroxy-2-(3'-aminophenyl)acetic acid (compound 10); (±)-2-hydroxy-2-(4'-aminophenyl)acetic acid (compound 11); (±)-2-hydroxy-3-(4'-aminophenyl)propionic acid (compound 21) and (±)-2-methoxy-2-(3'-aminophenyl)acetic acid (compound 22).

Further compounds contemplated for use in the disclosed methods: 5-aminosalicylo-hydroxamic acid (compound 5); 3-dimethylaminosalicylic acid (compound 6); 2-methoxy-4-aminobenzoic acid (compound 7); 2-methoxy-5-aminobenzoic acid (compound 8); 5-methylaminosalicylic acid (compound 9); 4-methylaminosalicylic acid (compound 12); 4-acetylaminosalicylic acid (compound 16); 2-ethoxy-4-aminobenzoic acid (compound 18); 2-ethoxy-5-aminobenzoic acid (compound 19); 4-dimethylaminosalicylic acid (compound 24); 2-ethoxy-4-aminobenzoylhydroxamic acid (compound 25); 6-hydroxyquinoline-5-carboxylic acid (compound 27); 2-(2-propyl)oxy-4-aminobenzoic acid (compound 30); 4-(1-piperazinyl)salicylic acid (compound 41); (R,S) 5-oxa-quinoline-6-carboxylic acid (compound 15); 6-methoxy quinoline-5-carboxylic acid (compound 36); 6-methoxy-1,2,3,4-tetrahydroquinoline-5-carboxylic acid (compound 37); 5-diisopropylaminosalicylic acid (compound 38); and 4-diisopropylaminosalicylic acid (compound 42).

Methods for making contemplated compounds may be found for example in WO2007/010516 and WO2007/010514, each hereby incorporated by reference in their entirety.

Therapeutic Applications

Methods of preventing or reducing colon carcinogenesis or colon cancer form part of this disclosure. Such methods may comprise administering to a patient, for example, a patient at risk of colorectal cancer, a pharmaceutical preparation comprising a chemopreventive agent such as those disclosed herein, e.g., compounds 17, 29, 39 or 34. A patient at risk of colon cancer or colon carcinogenesis may include those patients with ulcerative colitis, inflammatory bowel disease, or Crohn's disease. A patient at risk may also include those patients with an early age at diagnosis of Crohn's or colitis, extensive and/or severe of colonic disease, patients with the presence of primary sclerosing cholangitis, and/or patient's having a family history of cancer.

Patients treated using the above method may or may not have detectable colorectal cancer. In an different embodiment, spontaneous mutation frequency of a colon carcinoma cells may or may not be present in the patient before initial administration, or during the administration of a course, of a compound disclosed herein. In some embodiments, the patient has at least about a 5%, 10%, 20%, 30%, 40% or even 50% or more reduction of the mutation rate of colon carcinoma cells present in the patient after administering a disclosed compound, after e.g. 1 day, 2 days, 1 week, 1 month or 6 months or more. Without being bound by any theory, compounds disclosed herein may reduce mutation rate by interacting with cellular machineries involved in progression through the cell cycle. Such a progression may result in slowing down processes such as DNA replication (S phase) and/or cell division (mitosis) through the onset of cell cycle checkpoints, which would give the cell the opportunity to either repair the damage that the DNA may have encountered or undergo apoptosis. In both cases, this would prevent accumulation of mutated or damaged cells and would lead to maintenance of DNA integrity.

Also contemplated herein is a method for delaying clinical manifestation of a colorectal tumor, or a solid tumor (e.g., a breast, prostate, lung or hepatocellular carcinoma) in a patient, for example, a patient at risk of colorectal cancer, comprising administering to the patient an effective amount of a chemopreventive compound disclosed herein, e.g. compounds 17, 29, 39 or 34. Administering such a compound may be on e.g., at least a daily basis. The delay of clinical manifestation of a colorectal tumor in a patient as a consequence of administering a compound disclosed here may be at least e.g., 6 months, 1 year, 18 months or even 2 years or more as compared to a patient who is not administered a chemopreventive compound such as one disclosed herein.

Also forming part of this disclosure are methods of preventing or reducing solid tumors or adenocarcinomas, such as breast, cervix, pancreas, prostate adenocarcinomas and/or hepatocellular carcinomas. Such methods may comprise administering to a patient, for example, a patient at risk of such cancers, a pharmaceutical preparation comprising a chemopreventive agent such as those disclosed herein, e.g., compounds 17, 29, 39 or 34 disclosed herein.

Methods of treating a patient that is suffering from a disease where attenuation of oxygen free radicals is useful, for example, autoimmune, cardiovascular, and skin and/or hair disorders, comprising administering a disclosed compound (e.g., Formulas I, IIa, or IIb) are also contemplated herein.

For example, a method of treating hair loss in a patient suffering from unwanted hair loss, is contemplated, wherein the method comprises administering an effective amount of a composition comprising a disclosed compound, e.g. a compound of formula I, IIa or IIb (for example, compounds 17, 28, 29 34 or 14. Such a composition may be administered topically. Superoxide dismutase has been used as a treatment for hair loss, and in an embodiment, disclosed compounds having superoxide dismutase properties are contemplated for use in methods of treating hair growth and/or decreasing hair loss, e.g. such compounds when administered to a patient, e.g. topically, may increase the size of hair follicles and/or increase the rate of hair growth. Methods of treating alopecia areata, androgenetic alopecia and/or telogenic defluvium are contemplated.

Methods of protecting from and/or ameliorating free radical damage to the skin, comprising administering, e.g. administering topically, an effective amount of a composition comprising a compound disclosed herein, e.g., a compound of formula I, IIa or IIb is disclosed, e.g. compounds 17, 28, 29 34 or 14. Superoxide dismutase, for example, is known for such treatments (see e.g., J. Cell. Mol. Med. 8 (1): 109-116, (2007): "Topical superoxide dismutase reduces post-irradiation breast cancer fibrosis"; J. Derm Sci. Suppl 2(1) S65-S74, (2006)).

For example, the disclosed compounds may be used to reduce or ameliorate scar tissue of the skin, heal wounds and burns, protect skin against UV rays, and/or heal skin damaged from exposure to UV light. For example, disclosed compounds may be used to reduce fibrosis following radiation. Also contemplated are methods of treating fine lines, wrinkles or surface irregularities of the skin, comprising administering, e.g. administering topically, an effective amount of a composition comprising a compound disclosed herein, e.g., a compound of formula I, IIa or IIb (e.g., compounds 17, 28, 29 34 or 14).

Methods of treating dermatological conditions are also provided, such as the treatment of at least one of: acne vulgaris, comedo-type acne, polymorphic acne, acne rosacea, nodulocystic acne, acne conglobata, senile acne, secondary acne, solar acne, acne medicamentosa or occupational acne, ichthyosis, Darrier's disease, keratosis palmaris or plantaris, cutaneous, mucosal or ungual psoriasis, skin disorders due to exposure to UV radiation, of skin aging, photoinduced or chronological or actinic pigmentations and keratoses, acne hyperseborrhoea, simple seborrhoea or seborrhoeic dermatitis, cicatrization disorders or stretch marks, comprising administering an effective amount of a disclosed compound. Method of treating atopic dermatitis is also contemplated. The composition may be administered orally or topically.

Superoxide has been implicated in age-related diseases such as diabetes, cataracts, neurodegenerative diseases such as Alzheimer's disease and Parkinson's disease, macular degeneration, retinal ulcers and/or retinal vasculitis, and prostate cancer. (See e.g., "Antioxidants, diabetes and endothelial dysfunction." Cardiovascular Research, 47(3) 457-464, 2000; Role of anti-oxidant enzymes superoxide dismutase and catalase in the development of cataract: study of serum levels in patients with senile and diabetic cataracts", J Indian med Assoc. 104(7): 394, 396-7, 2006; "Oxidative stress hypothesis in Alzheimer's disease", Free Radical Biology and Medicine, 23(1): 134-147, 1997; "Oxidative mechanisms in nigral cell death in Parkinson's disease." Mov Disord. 1998; "Involvement of oxidative and nitrosative stress in promoting retinal vasculitis in patients with Eales' disease" Clinical Biochemistry, 36(5): 377-385, 2003; Contemplated herein are methods of treating such age-related disorders such as diabetes, cataracts, neurodegenerative diseases such as Alzheimer's disease and Parkinson's disease, macular degeneration, retinal ulcers and/or retinal vasculitis, comprising disclosed compounds. For example, methods of ameliorating, reducing the effects of, or preventing macular degeneration are provided herein comprising administering a compound represented by Formula I, IIa or IIb (for example, compounds 17, 28, 29, or 34).

In an embodiment, methods are provided for treating oxidative stress in patients in need thereof, comprising administering compounds disclosed herein. For example, a method of treating hypoxia is provided comprising administering to a patient in need thereof a compound disclosed herein.

Oxidative stress may result, for example, from the metabolic reactions that use oxygen, and in some embodiments, can describe a disturbance in the equilibrium status of pro-oxidant/anti-oxidant systems in intact cells. Oxidative stress has been implicated, for example, in cardiac and vascular disorders and diseases such as chronic coronary ischemia, arteriosclerosis, congestive heart failure, angina, atherosclerosis, myocardial infarction, stroke and myocardial hypertrophy. For example, a method of treating or inhibiting an ischemic or reperfusion related injury in a patient in need thereof is provided, comprising administering to the patient a composition comprising an effective amount of compound of formula I, IIa, or IIb. Methods are provided herein for treating such cardiac and/or vascular disorders in a patient in need thereof comprising administering a disclosed compound, e.g. a compound represented by formula I, IIa or IIb. A method for treating chronic obstructive pulmonary disorder is also provided, comprising administering a disclosed compound, e.g. a compound represented by formula I, IIa or IIb, e.g., compounds 17, 28, 29 34 or 14

Methods for treating autoimmune disorders are also contemplated, for example, methods of treating Addison's disease, chronic thyroiditis, dermatomyositis, Grave's disease, multiple sclerosis, systemic lupus erythematosis, psoriasis, or rheumatoid arthritis, comprising administering to a patient in need thereof an effective amount of a compound of formula I, or e.g. compounds 17, 28, 29 34 or 14.

Generally, a therapeutically effective amount of active component will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the binding protein delivered, the formulation of the binding protein, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks.

Contemplated formulations or compositions comprise a disclosed compound and typically include a compound a pharmaceutically acceptable carrier.

Compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, film-coated tablets, sugar-coated tablets, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Formulations and compositions may include micronized crystals of the disclosed compounds. Micronization may be performed on crystals of the compounds alone, or on a mixture of crystals and a part or whole of pharmaceutical excipients or carriers. Mean particle size of micronized crystals of a disclosed compound may be for example about 5 to about 200 microns, or about 10 to about 110 microns.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as film coated tablets or sugar coated tablets, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal or topical administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. The efficacy of treatment with the subject compositions may be determined in a number of fashions known to those of skill in the art.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Except where indicated otherwise, the order of steps or order for performing certain actions are immaterial so long as the invention remains operable. Moreover, unless otherwise noted, two or more steps or actions may be conducted simultaneously.

EXAMPLES

Example 1 Superoxide Scavenging

Compounds 17 and 39 were tested for their potential to scavenge superoxide ($O_2^-$) released by activated neutrophils (PMN) using a standardized $O_2^-$ assay. Briefly, $1\times10^6$ freshly isolated neutrophils were activated with phorbol-myristate-acetate (PMA) in absence or presence of the compounds (each 5 mM). 30 min after activation the $O_2^-$ release was measured by lucigenin amplified chemiluminescence on a luminometer. 5-ASA (5-aminosalicylic acid) and superoxide dismutase (SOD) was used as a control. Experiments were done in triplicates.

At 5 mM, compound 17 acts as a strong scavenger of superoxide (5% of control), being as active as a mixture of superoxide dismutase and catalase. Compound 39 has similar scavenging properties to 5-ASA, as shown in FIG. 1.

Example 2 Superoxide Scavenging

Figure 2A:
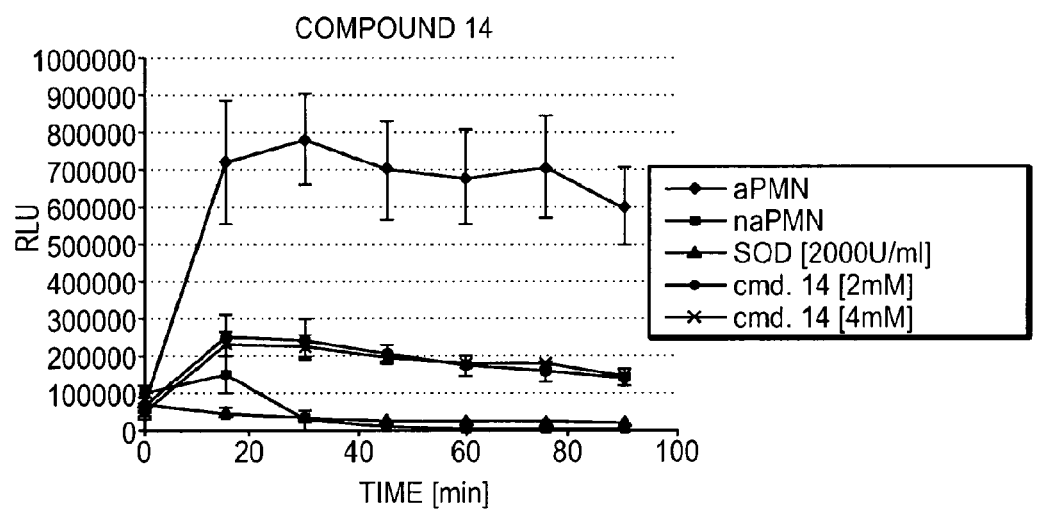
FIGS. 2A and 2B depict superoxide scavenging properties of compounds disclosed herein.
Figure 2B:
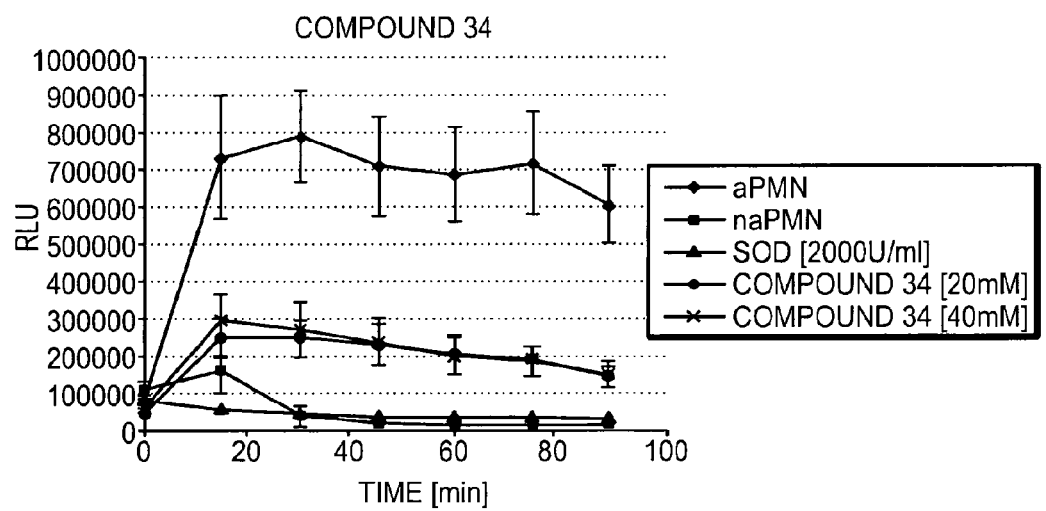

Compounds 14 and 34 were tested for their potential to scavenge superoxide ($O_2^-$) released by activated neutrophils (PMN) using a standardized $O_2^-$ assay, similar to Example 1. Activated neutrophils (PMN) were used as $O_2^-$ donors. Briefly, $1\times10^6$ freshly isolated neutrophils were activated with 100 nM phorbol-myristate-acetate (PMA). The $O_2^-$ release was measured every 15 min for a 90 min period by lucigenin amplified chemiluminescence on a luminometer. Either non-activated PMNs or activated PMNs incubated with superoxide dismutase (2000 U/ml, SOD) was used as a control. Experiments were carried out in triplicates At the investigated concentrations both compounds exhibited significant scavenging properties. FIG. 2A represents the results for compound 14, and FIG. 2B represents the results for compound 34.

Example 3 Replication Fidelity

A EGFP-based assay to determine the changes in mutation rate upon incubation with various concentrations of the compounds was used to test whether compounds improve the replication fidelity. Briefly, $1\times10^3$ EGFP negative HCT116 A2.1 cells were sorted into 24-well plates on a FACS Aria. 24 hours later cells were treated with the compounds for a period of 7 days and the mutant fraction was measured by flow cytometry.

Figure 3C:
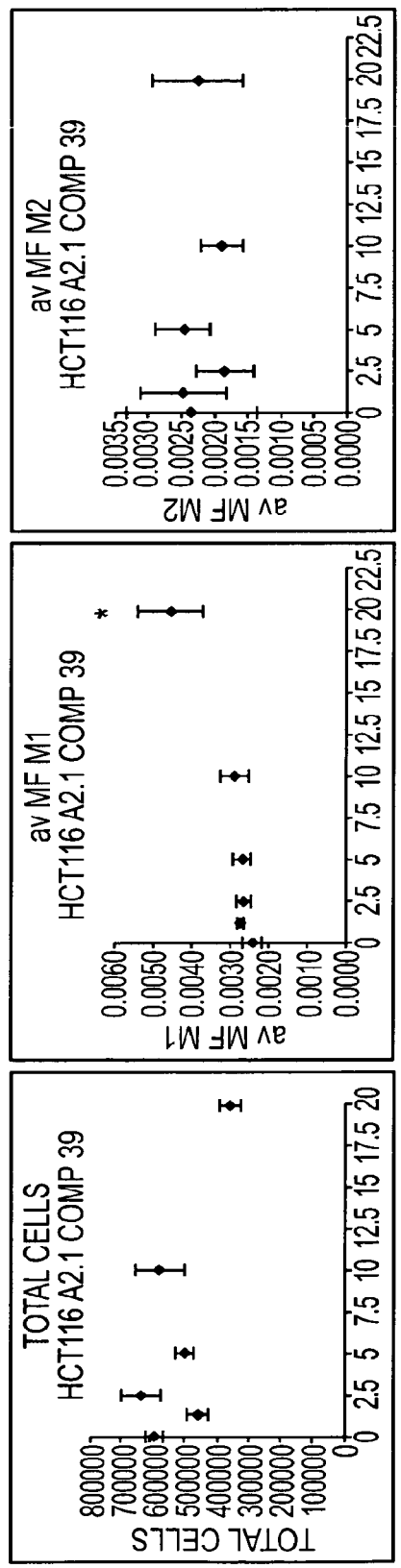

Compound 17 affects cell growth already at low concentrations starting from 1.25 mM. Surprisingly, compound 17 leads to a 50% reduction of the intermediate mutant cells (M1 population) at a concentration of 5 mM. Furthermore compound 17 led to about a 30% reduction of definitive mutant cells (M2 population) at concentrations between 2.5 and 5 mM (FIG. 3A)

FIG. 3B indicates that compound 28 does not appear to cause significant changes at concentrations up to 1 mM.

Compound 39 reduced cell growth at 20 mM but did not reduce the mutant fraction M1 or M2. Instead, treatment with 20 mM compound 39 leads to an increase of M1 (FIG. 3C), comparable to the effect of aspirin.

Among the tested compounds 17, 28 and 39, compound 17 exhibits positive effects on the replication fidelity in HCT116 cells harboring a (CA)13 repeat. This effect is not only seen in the intermediate mutant fraction M1 but also in the definite mutants M2. Compound 17 is also the strongest scavenger. This reduction of M1 or M2 does not seem to depend on an S-phase arrest (as it was seen with 5-ASA; Luciani G, Gastroenterology 2007).

Example 4

A EGFP-based assay similar to Example 3 was used to determine the changes in mutation rate upon incubation with various concentrations of disclosed compounds and to test whether the compounds improve the replication fidelity. A EGFP based assay was used to determine the changes in mutation rate at a (CA)13 repeat upon incubation with various concentrations of the compounds. Briefly, $1\times10^3$ EGFP negative HCT116 A2.1 cells were sorted into 24-well plates on a FACS Aria. 24 hours later cells were treated with the compounds for a period of 7 days. The total cell number (c) and the EGFP-positive fraction (mutant fraction (MF)) were analyzed by flow cytometry. The mutation rate (m/(CA)13/generation (gen)) was estimated by m=MF/(gen+1) and gen=log $2(c/1000\times cloning$ efficiency). The transient mutant (M1) and definitive mutant (M2) cells were distinguished.

Figure 4:
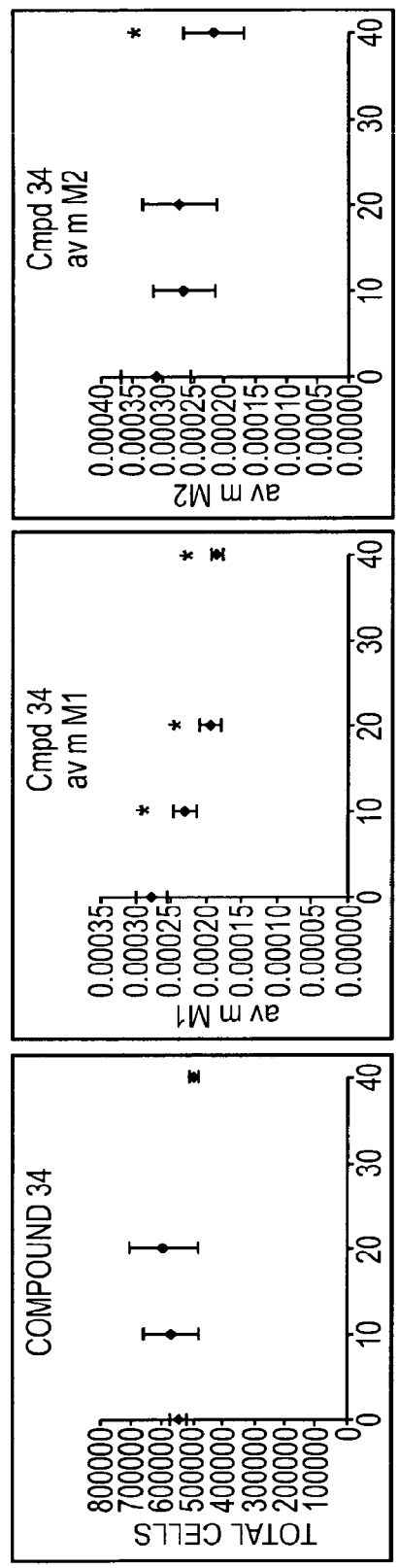
FIG. 4 depicts the changes in mutations rate of HCT116 A2.1 cells upon incubation with various concentrations (mM) of a compound disclosed herein.

As shown in FIG. 4, compound 39 significantly lowered the number of M1 cells, which reflects a population of cells immediate after the polymerase error in MMR deficient HCT116 cells starting at a concentration of 10 mM up to 40 mM ($p<0.05$). There was also a significant reduction in the permanent mutant M2 population at 40 mM.

Example 5 Cell Cycle Analysis

BrdU staining was used to analyze cell cycle changes in HCT116 and HT29 cells upon 72 hour treatment with compound 39. Data represent the mean values of 3 independent experiments (* indicates a $p<0.05$ compared to control)

Figure 5A:
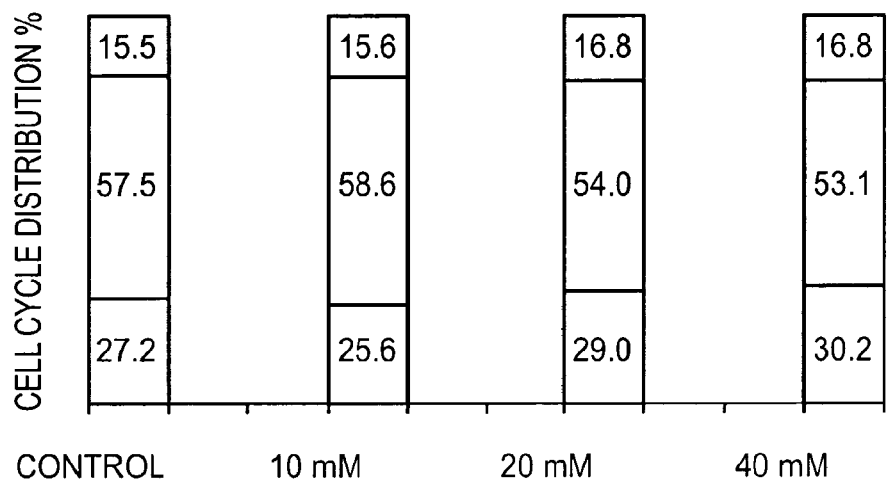
FIGS. 5A and 5B depict the cell cycle changes in HCT116 and HT29 cells upon treatment with a compound disclosed herein.
Figure 5B:
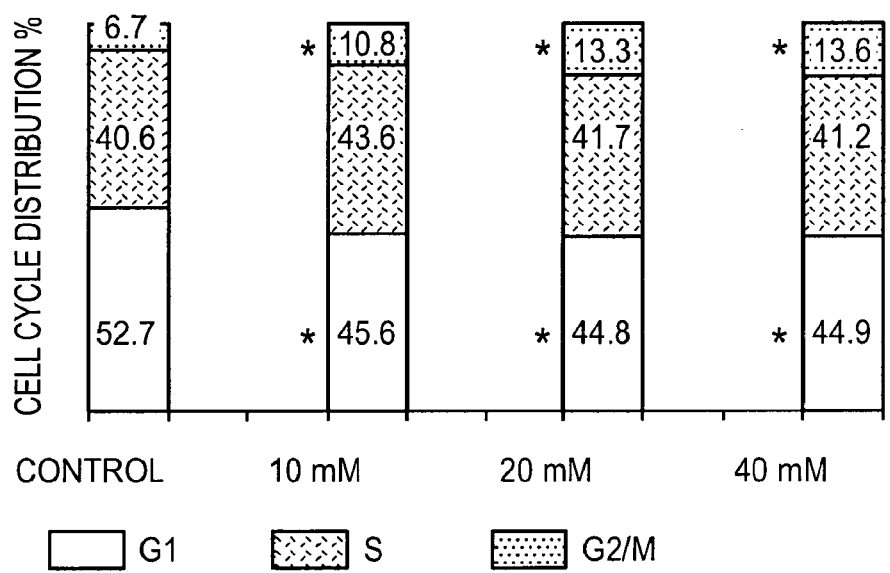

Compound 39 (10 mM-40 mM) did not induce a significant change in the cell cycle distribution of HCT116 cells. HT29 cells revealed a mild increase in the G2 phase (ranging from 6.7% to 13.6%, $p<0.05$) which was paralleled by a decrease in the G1 population (ranging from 52.7% to 44.9%, $p<0.05$) (FIGS. 5A and 5B).

Example 6 Cell Proliferation

The inhibitory effect on cell proliferation of compound 34 using MTT assay was investigated. Briefly, $5\times10^3$ HCT116, HCT116+chr3, HT29 and Lovo cells were incubated for 72 hours in 96-well plates with various concentrations. Compound 34 is soluble in IMDM. Stocks of 100 mM were prepared and the pH was adjusted to 7.4.

Figure 6:
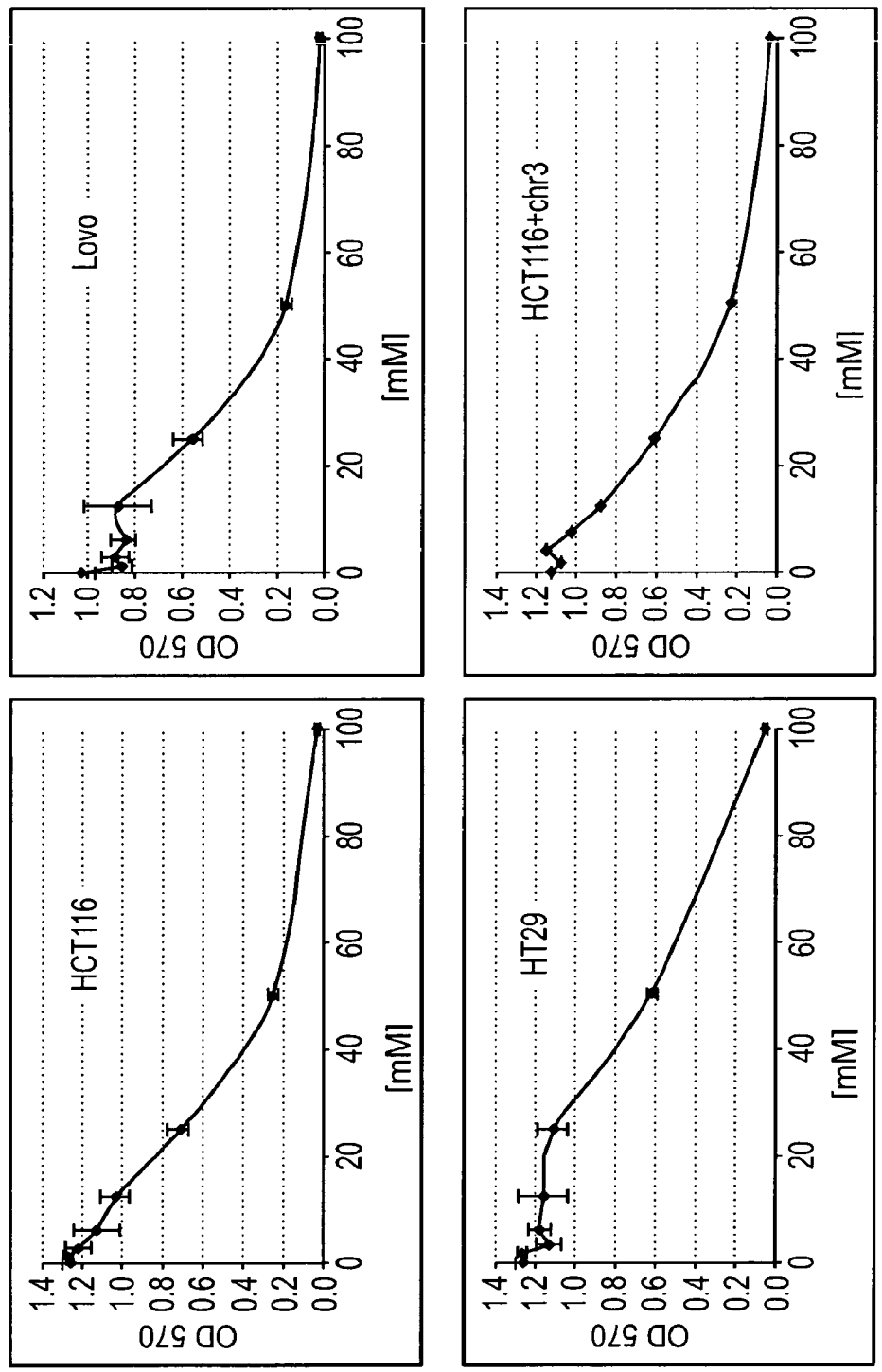
FIG. 6 depicts the effect on cell proliferation in HCT116, HCT116+chr3, HT29 and Lovo cells using a compound disclosed herein.

FIG. 6 indicates that compound 34 has an $IC_{50}$ at 30-40 mM dependent on the cell type.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

We claim:

1. A method of treating psoriasis, the method comprising administering orally to a patient in need thereof an effective amount of 2-methoxy-3-(4'-aminophenyl) propionic acid, or a pharmaceutically acceptable salt or a stereoisomer thereof.

2. The method of claim 1, wherein the stereoisomer is (S)-2-methoxy-3-(4'-aminophenyl) propionic acid, or a pharmaceutically acceptable salt thereof.

* * * * *